US007173017B1

(12) United States Patent
von Borstel et al.

(10) Patent No.: US 7,173,017 B1
(45) Date of Patent: Feb. 6, 2007

(54) PYRIMIDINE NUCLEOTIDE PRECURSORS FOR TREATMENT OF SYSTEMIC INFLAMMATION AND INFLAMMATORY HEPATITIS

(75) Inventors: Reid W. von Borstel, Potomac, MD (US); Michael K. Bamat, Potomac, MD (US); Bradley M. Hiltbrand, Columbia, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 0 days.

(21) Appl. No.: 08/465,455

(22) Filed: Jun. 5, 1995

Related U.S. Application Data

(60) Division of application No. 08/266,897, filed on Jul. 1, 1994, now abandoned, which is a continuation-in-part of application No. 08/158,799, filed on Dec. 1, 1993, now abandoned, which is a continuation-in-part of application No. 07/987,730, filed on Dec. 8, 1992, now abandoned, which is a continuation-in-part of application No. 07/438,493, filed as application No. PCT/US88/03823 on Oct. 27, 1988, now abandoned, which is a continuation-in-part of application No. 07/115,929, filed on Oct. 28, 1987, now abandoned.

(51) Int. Cl.
*A61K 31/70* (2006.01)
(52) U.S. Cl. .......................... 514/50; 514/49
(58) Field of Classification Search ............... 514/49, 514/50
See application file for complete search history.

(56) References Cited

U.S. PATENT DOCUMENTS

| 3,161,565 A | 12/1964 | Vigneron |
| 3,868,451 A | 2/1975 | Stein et al. |
| 4,027,017 A | 5/1977 | Hata et al. |
| 4,058,601 A | 11/1977 | Hata et al. |
| 4,613,604 A | 9/1986 | Chu et al. |
| 4,757,139 A | 7/1988 | Kawaguchi et al. |
| 4,874,602 A | 10/1989 | Calabresi et al. |
| 5,077,280 A | 12/1991 | Sommadossi et al. |
| 5,141,943 A | 8/1992 | Naguib et al. |
| 5,298,487 A | 3/1994 | Chen et al. |

FOREIGN PATENT DOCUMENTS

| AU | 27226/88 | 5/1989 |
| AU | 22544/92 | 1/1993 |
| EP | 339075 B1 | 11/1989 |
| EP | 355131 B1 | 2/1990 |
| EP | 0 358 008 A1 | 3/1990 |
| GB | 1 297 398 | 11/1972 |
| JP | 60-174797 | 2/1984 |
| JP | 2-500372 A | 2/1990 |
| JP | 03/135918 | 6/1991 |
| JP | 3-169815 | 7/1991 |
| WO | WO 85/00608 | 2/1985 |
| WO | WO80/03837 | 5/1989 |
| WO | WO80/03838 | 5/1989 |
| WO | WO 89/03837 | 5/1989 |
| WO | WO 89/03838 | * 5/1989 |
| WO | 94/13687 | 6/1994 |
| WO | WO 94/13687 | 6/1994 |

OTHER PUBLICATIONS

Baker et al., American J. of Medicine, vol. 82(3), 1987.*
Aderka et al, "Med Hypotheses", (1988), 27:193-6.
Arai M. et al, "Hepatology" (1989) 9:846-851.
Bowers et al., "J. Surg. Res." (1989) 47:183-8.
Cerra et al, in "Molecular and Cellular Mechanisms of Septic Shock" 265-277, Alan R. Liss (1989).
Clark et al, "Am. J. Pathol." (1987), 129:192-9.
Echtenacher et al, "J. Immunol." 145:3762-3766 (1990).
Engelhardt, R. et al, "Cancer. Res." (1991), 51:2524-30.
Farrar and Corwin, Ann. "N.Y. Acad. Sci." 133:668-684 (1966).
Galanos et al, "PNAS", 76:5939-5943, (1979).
Gut et al, "J. Infect. Disease." (1984) 149:621.
Halacheva et al, "Toxicon" (1988), 26:571-576.
Havell, "J. Immunol." 139:4225-4231 (1987).
Kang et al, "J. Histochem. Cytochem." (1988), 36:665-678.
Kilpatrick et al, "Metabolism" (1989) 38:73-7.
Kimura et al, "Cancer, Chemother, Pharmacol" (1987); 20:223-9.
Lomanto et al, "Anesth. Analg." (1972), 51:264-270.
Markley et al, "J. Trauma" 10:598-607, (1970).
McClain CJ and Cohen DA, "Hepatology" (1989) 9:349-351.
Nolan JP, "Gastroenterology" 69:1346-1356 (1975).
Nolan, JP, "Hepatology" (1989), 10:887-91.
Nolan JP and Leibowitz AI, "Gastroenterology" (1978), 75:445-9.
O'Sullivan, "Aust. N.Z. J. Med.", (1973) 3:417-422.
Pappo et al, "J. Surg. Res." (1991) 51:106-12.
Pates et al, "Farmakol Toksikol" (1968), 31:717-719.
Rosenthal et al, "Toxicology" 56:239-251 (1989).
Seljelid, "Scand. J. Immunol." (1989), 29:181-92.
Shafer et al "Gastroenterology" (1961), 40:782-784.
Shirai et al"Acta Pathol. Jpn." (1987) 37:1127-1134.
Taki et al "Eur. Surg. Res." (1985), 17:140-9.
Tiegs et al "J. Clin. Invest." (1992) 90:196-203.
Van Bladel et al "Cytokine" (1991) 3:149-54.
van Groeningen et al "Proceedings of the AACR" (1987), 28:195.
Van Groeningen et al "Cancer Tret Rep." (1986), 70:745-50.
Viens et al "J. Immunother" (1992), 11:218-24.
Von Euler et al "J. Biol. Chem." (1963), 238:2464-2469.
Wang et al "Arch. Surg." (1991), 126:219-224.
Lehninger, Albert L., "Biochemistry" Second Edition, Worth Publishers, Inc. New York, 1975, pp. 735-736.
—Martin et al., J. Pharm. Sci., V. 76, No. 2 (Feb. 1987) p. 180-183 "Synthesis And Antiviral Activity of Various Esters of 9-[1,3-Dihydroxy-2-propoxy)methyl]guanine."
—Casida et al, Biochemical Pharmacology, V. 15, (1966) p. 627-644 "3',5'-Diesters of 5-Fluoro-2'-Deoxyuridine and Thymidine: Hydrolysis by Esterases in Human, Mouse, and Insect Tissue."

(Continued)

*Primary Examiner*—Elli Peselev
(74) *Attorney, Agent, or Firm*—Nixon & Vanderhye

(57) ABSTRACT

Pyrimidine nucleotide precursors including acyl derivatives of cytidine, uridine, and orotate, and uridine phosphorylase inhibitors, and their use in enhancing resistance to sepsis or systemic inflammation are disclosed.

5 Claims, No Drawings

OTHER PUBLICATIONS

—Ensminger et al, Biochemical Pharmacology, V. 28 (1979) p. 1541-1545 "Thymidine 5'-O-Pivaloate: A Prodrug Derivative of Thymidine with Potential Applications in High-Dose Methotrexate Therapy."

—Martin et al, Cancer Research, V. 42 (Oct. 1982) p. 3964-3970 "High-Dose 5-Fluorouracil with Delayer Uridine 'Rescue' in Mice."

Derwent Abstract No. 91-212578 of Japanese Publication JO 3135918 (Ajinomoto) (1991).

Tsujinaka et al., "Role of nucleosides and nucleoside mixture in Intestinal Mucosal Growth Under Parenteral Nutrition", Nutrition (Nov.-Dec. 1993) 9(6):532-5.

Translation of Office Action mailed Jun. 1, 2004 in counterpart Japanese Patent Application No. 510442/94.

Bamat, M.K., et al; "Acylated Uridine and Cytidine and Uses Thereof"; (1989); Patent No. WO/8903837; (Abstract not Available).

Kypson, J. et al; "Effects of Uridine and Indosine on Glucose Metabolism in Skeletal Muscle and Activated Lipolysis in Adipose Tissue"; *The Journal of Pharmacology and Experimental Therapeutics*; vol. 199, No. 3; pp. 565-574; XP-008033089 (1976).

Nelson, K.A., et al; "The Cancer Anorexia-Cachexia Syndrome"; *Journal of Clinical Oncology*; vol. 12, No. 1; pp. 213-225; XP-002054945 (1994).

Bruera, E.; "Clinical Management of Anorexia and Cachexia in Patients with Advanced Cancer"; *Oncology*; vol. 49, No. Suppl 2; pp. 35-42; XP-001037960 (1992).

Tisdale, M.J.; "Cancer Cachexia"; *Anti-Cancer Drugs, Rapid Communications, Oxford Ltd.*; vol. 4, No. 2; pp. 115-125; XP-009023231 (1993).

Berkow, R.; "The Merck Manual of Diagnosis and Therapy, 15th ed."; *Merck Sharp & Dohme Research Laboratories*; pp. 907-911 (1987); XP-002276510.

Ogoshi, S., et al; "Effects of Total Parenteral Nutrition with Nucleoside and Nucleotide Mixture on D-Galactosamine-Induced Liver Injury in Rats"; *Journal of Parenteral and Enteral Nutrition*; vol. 12, No. 1; pp. 53-57 (1988); XP-008029611.

Wang, J., et al; "Studies on the Hepatotoxicity of Galactosamine/Endotoxin or Galactosamine/TNF in the Perfused Mouse Liver"; *Biochemical Pharmacology*, vol. 39, No. 2, pp. 267-270 (1990); XP-001189750.

Yokoyama, H., et al; "A Nucleoside Mixture and its Sparing Effect on *De Novo* Purine Nucleotide Synthesis"; *Advances in Experimental Medicine and Biology* (1994), 370(Purin and Pyrimidine Metabolism in Man VIII, pp. 541-544; XP-008029609.

Kambara, Y., et al; Chemical Abstracts Service, Columbus, OH; "The Effect of Nucleosides and Nucleotides on Liver Regeneration"; Database Accession No. 108:185605; XP-002276511 (Abstract).

Bushma, M. et al.; U.S. National Library of Medicine (NLM); Bethesda, MD; (1979); "The Effect of Cytidine and Uridine on Liver Regeneration in Rats Poisioned by Carbon Tetrachloride"; Database Accession No. NLM519007; XP-002276512 (Abstract).

MacDonald, J.R., et al; Biosciences Information Service, Philadelphia, PA, (1987); "Inhibition of Galactosamine Cytotoxicity in an In-Vivo-In-Vitro Hepatocellular Toxicity Model"; Database Accession No. PREV198784072284; XP-002276513 (Abstract).

Takeda, S. et al; Biosciences Information Service, Philadelphia, PA; (1985); "Pharmacological Studies on Schizandra Fruits 3. Effects of Wuweizisu C.A. Lignan Component of Schizandra Fruits on Experimental Liver Injuries in Rats"; Database Accession No. PREV198580043139; XP-002276514 (Abstract).

Decker, K. et al; "Galactosamine Induced Livery Injury"; *Progress in Liver Diseases*; (1972); vol. 4, pp. 183-199; XP-008029633.

Patent Abstracts of Japan, vol. 017, No. 270; May 26, 1993; JP 05 009121 A (Otsuka Pharmaceut Factory Inc); Jan. 19, 1993 (Abstract).

Tsujinaka et al.; "Role of nucleosides and nucleotide mixture in Intestinal Mucosal Growth Under Parenteral Nutrition"; *Nutrition* vol. 9, No. 6; pp. 532-5 (1993).

\* cited by examiner

PYRIMIDINE NUCLEOTIDE PRECURSORS FOR TREATMENT OF SYSTEMIC INFLAMMATION AND INFLAMMATORY HEPATITIS

This is a Divisional of application Ser. No. 08/266,897, filed Jul. 1, 1994 now abandoned; which in turn is a CIP of Ser. No. 08/158,799, filed Dec. 01, 1993 now abandoned; which is a CIP of Ser. No. 07/987,730, filed Dec. 08, 1992, now abandoned; which is a CIP of Ser. No. 07/438,493, filed Jun. 26, 1990 now abandoned; which is a 371 of PCT/US88/03823, filed Oct. 27, 1988, which is CIP of Ser. No. 07/115,929, filed Oct. 28, 1987 now abandoned.

FIELD OF THE INVENTION

This invention relates generally to pyrimidine nucleotide precursors including acyl derivatives of cytidine, uridine and orotate, and to the prophylactic and therapeutic uses of these compounds. The invention also relates to the administration of these compounds, alone or in combinations, with or without other agents, to animals. These compounds are capable of enhancing resistance of an animal to bacterial endotoxin and other inflammatory stimuli, and inflammatory mediators.

BACKGROUND OF THE INVENTION

Sepsis, also referred to as sepsis syndrome, is a consequence of serious infection by bacteria, fungi, or viruses. Sepsis accounts for tens of thousands of deaths in the United States every year; it is a leading cause of death of patients in surgical intensive care units.

Sepsis is an inflammatory disorder in which endogenous cytokines and other bioactive molecules, produced or released in response to an inflammatory stimulus such as bacterial endotoxin (a component of the cell wall of gram-negative bacteria), cause various symptoms including fever, neutropenia, blood coagulation disorders, hypotension, shock, and organ damage.

Sepsis (or in its more severe form, septic shock), is one example of a broader class of disease called the "Systemic Inflammatory Response Syndrome" (SIRS), which is an organism's reaction to inflammatory stimuli such as endotoxin (which can be present in the bloodstream without bacteremia, e.g. due to leakage of endotoxin from gram-negative bacteria into the circulation from a localized infection or from the intestine); SIRS can also be triggered by gram-positive bacteria, fungi, viruses, and can also be a consequence of autoimmune disorders or administration of therapeutic inflammatory cytokines.

Current treatment of SIRS involves circulatory and respiratory support, but does not directly address improvement of tissue resistance to inflammatory stimuli such as endotoxin, or inflammatory mediators.

Monoclonal antibodies for neutralizing endotoxins or mediators of its physiologic effects are under development. However, it is expensive or impractical to use antibodies as prophylaxis in susceptible patients, prior to the onset of symptoms of endotoxin poisoning. Moreover, it is difficult to determine which patients are likely to benefit from antibody treatment, since the time required to culture and identify infectious organisms often exceeds the time limit for implementation of effective therapy. Similar problems have been encountered in attempts to use receptor antagonists of specific inflammatory meidators like interleukin-1.

Endotoxin toxicity is in part mediated by endogenous cytokines and other bioactive molecules released from macrophages, Kupffer cells (sessile macrophages in the liver) and other cell types in response to endotoxin. Among the most significant of these mediators are tumor necrosis factor (TNF) and interleukin-1 (IL-1). Others include platelet activating factor (PAF), interleukin-6, and leukotrienes and other arachidonic acid derivatives. Administration of these cytokines or mediators results in symptoms similar to at least some of those elicited by endotoxin. Agents or pathological conditions other than bacterial endotoxin can result in elevated production or activity of (or sensitivity to) TNF or IL-1, resulting in tissue damage. Such conditions include infection with gram-positive bacteria, viruses or fungi, or liver damage. Inflammatory cytokines can produce tissue damage if present in excess, but when elicited in moderate amounts, they are important in the defense against infectious organisms or viruses. For example, antibodies to TNF can reduce toxicity of an administered dose of endotoxin (by blocking the negative effects of TNF elicited by the endotoxin), but can have a deleterious effect in the case of some bacterial infections, converting a sublethal state of infection into an overwhelming lethal infection (Havell, *J. Immunol.*, 1987, 139:4225–4231; Echtenacher et al., *J. Immunol.*, 1990 145:3762–3766). Thus, there are inherent problems with strategies for treating sepsis syndrome or SIRS with agents which directly inactivate inflammatory cytokines.

The liver is a major site for clearance or detoxification of endotoxin (Farrar and Corwin, Ann. *N.Y. Acad. Sci.,* 1966 133:668–684) and inflammatory proteins like TNF; conversely, the liver is susceptible to damage by endotoxin and its mediators. Liver damage from many originating causes (e.g. carbon tetrachloride, choline deficiency, viral infection, Reye's syndrome, alcohol) is in part mediated by bacterial endotoxin or mediators elicited by endotoxin even when symptoms of systemic sepsis are not present (Nolan, *Gastroenterology,* 1975, 69:1346–1356; Nolan, *Hepatology,* 1989, 10:887–891). Hepatic toxicity is dose-limiting in patients receiving intentional injections of endotoxin for possible efficacy in treating cancer (Engelhardt et al., *Cancer Research,* 1991, 51:2524–2530). The liver has been reported to be the first vital organ displaying pathological alterations in septic shock (Kang et al., *J. Histochem. Cytochem.,* 1988 36:665–678). Moreover, hepatic dysfunction occurs in the early stages of sepsis and may initiate sequential organ failure (Wang et al., *Arch. Surg.,* 1991, 126:219–224)

The liver is important in regulating the sensitivity of an animal to endotoxin. Various treatments which impair liver function or metabolism, such as poisoning with lead acetate, cycloheximide, Actinomycin D or galactosamine can increase the sensitivity of animals to endotoxin or TNF, in some cases by several orders of magnitude.

Galactosamine-induced liver damage is unique in that it is readily reversible during a period before cell death occurs. Galactosamine selectively depletes hepatic uridine nucleotides, by locking them into UDP-hexosamines that are not converted back into free nucleotides. This can lead to liver damage if the depletion of uridine nucleotides is sufficiently prolonged, due to impairment of RNA and protein synthesis. The biochemical deficiency induced by galactosamine is readily reversed by administration of uridine, which replenishes the uridine nucleotides trapped by the galactosamine. Thus, administration of uridine shortly before or after administration of galactosamine attenuates galactosamine-induced hepatic damage and consequently restores sensitivity to endotoxin toward normal values (Galanos et al., *PNAS*, 1979, 76:5939–5943).

Similarly, endotoxin hypersensitivity in mice deliberately treated with the rodent hepatotoxin TCDD was partially reversed by administration of uridine (Rosenthal et al., *Toxicology*, 1989 56:239–251).

However, in contrast to these situations wherein uridine partially reversed experimentally-reduced resistance to endotoxin, uridine was reported to have no protective effect in normal mice challenged with endotoxin (Markley et al., *J. Trauma* 1970, 10:598–607), i.e., it did not result in greater-than-normal resistance to endotoxin.

Uridine, cytidine, and orotate have been tested for effects on liver function in hepatic disorders and in experimental models, with mixed results. Shafer and Isselbacher (*Gastroenterology*, 1961, 40:782–784) reported that daily intravenous infusion of 25 to 100 milligrams of cytidine and uridine, for 3 to 7 days, to patients with hepatic cirrhosis had no effect on clinical status. Orotic acid added to rat diet in a concentration of 1 percent results in fatty infiltration of the liver (von Euler et al, *J. Biol. Chem.*, 1963, 238:2464–2469); orotic acid administered by intraperitoneal injection reduced liver damage in rats treated with carbon tetrachloride, dichloroethane, DDT, and 9,10-dimethyl-1,2-benzanthracene (Pates et al., *Farmakol Toksikol.*, 1968, 31:717–719). Lysine-orotate potentiated the toxicity of hepatotoxic extracts from the mushroom Amanita Phalloides; sodium orotate and orotic acid had no effect on Amanita extract toxicity (Halacheva et al., *Toxicon*, 1988, 26:571–576). Orotic acid has been administered clinically to humans for treatment of neonatal hyperbilirubinemia and for improving recovery from myocardial infarction (O'Sullivan, *Aust. N.Z. J. Med.*, 1973, 3:417–422). Orotate is not well absorbed after oral administration, in part due to poor solubility.

Hata et al. (U.S. Pat. Nos. 4,027,017 and 4,058,601) disclose that uridine diphosphate and uridinediphosphoglucuronic acid reduce blood alcohol content and inhibit accumulation of neutral lipids in the liver after administration of ethanol.

Clinical trials involving the administration of uridine (e.g. for the purpose of attenuating host toxicity of the antineoplastic drug 5-fluorouracil) have been complicated due to the biological properties of uridine itself. Uridine is poorly absorbed after oral administration; diarrhea is dose limiting in humans (van Groeningen et al., *Proceedings of the AACR*, 1987, 28:195). Parenteral administration of uridine requires use of a central venous catheter (with consequent discomfort and risk of infection), since phlebitis was a problem in early clinical trials when uridine was administered via a brachial venous catheter (van Groeningen et al. *Cancer Treat Rep.*, 1986, 70:745–50).

Administration of acyl derivatives of uridine and cytidine, which are readily absorbed from the gut into the bloodstream, and which are then hydrolyzed to yield free uridine or cytidine in the circulation, overcome the problem of poor oral absorption of the free nucleosides (U.S. patent applications Ser. Nos. 438,493, 115,929, and 903,107, hereby incorporated by reference).

OBJECTS OF THE INVENTION

It is a primary object of the invention to provide therapeutic and prophylactic agents which are effective in improving survival and in preventing tissue damage from systemic inflammatory response syndrome, including sepsis.

It is a primary object of this invention to provide a family of compounds which effectively enhance resistance to systemic inflammation. Administration of these compounds to an animal before, during or after exposure to endotoxin or other inflammatory stimuli, prevents or treats the effects of systemic inflammation.

It is a further object of this invention to provide a family of compounds for the treatment of a variety of disorders involving inflammatory stimuli or inflammatory cytokines in their etiology.

It is a further object of this invention to provide a family of compounds to improve survival or physiological functions in animals subjected to endotoxin poisoning or other systemic inflammatory disorders.

It is a further object of the invention to provide a family of compounds to treat or prevent inflammatory hepatitis.

It is a further object of the invention to provide compounds which can be administered orally or parenterally.

SUMMARY OF THE INVENTION

These and other objects of the invention are achieved by precursors of pyrimidine nucleotides such as orotic acid or its salts, uridine, cytidine, or prodrug derivatives of these agents including acyl derivatives or phosphate esters, which can be administered to animals, including mammals such as humans. The administration of these compounds alone, or in combination, is useful in treatment or prevention of consequences of systemic inflammation. Systemic inflammation is caused by infection with bacteria, fungi, or viruses, constituents of bacteria, fungi or viruses, e.g. endotoxin, polysaccharides or viral proteins respectively, by inflammatory mediators, or as a consequence of autoimmune disorders.

Thus, the compounds of the invention, alone or in combination, are useful in the treatment and prevention of sepsis or toxic effects of inflammatory cytokines; are useful as prophylactic agents in patients at risk of sepsis e.g. patients undergoing surgical procedures, or afflicted with serious burns or wounds, or immunocompromised as a consequence of chemotherapy for cancer or other diseases.

An important aspect of this invention is the discovery that pyrimidine nucleotide precursors such as orotate, uridine, or cytidine, and acyl derivatives of such compounds, have unexpected therapeutic properties.

One embodiment of the invention involves the use of the compounds and compositions of the invention in treatment and prevention of toxicity encountered during therapeutic administration of inflammatory cytokines, e.g. for treatment of cancer.

One embodiment of the invention involves the use of the compounds and compositions of the invention in treatment and prevention of inflammatory hepatitis.

COMPOUNDS OF THE INVENTION

The compounds useful in enhancing resistance to inflammatory stimuli or inflammatory mediators have the following structures:

In all cases except where indicated, letters and letters with subscripts symbolizing variable substituents in the chemical structures of the compounds of the invention are applicable only to the structure immediately preceding the description of the symbol.

(1) Uridine or an acyl derivative of uridine having the formula:

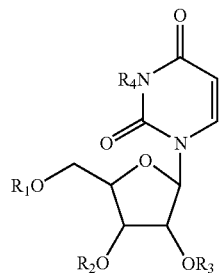

wherein $R_1$, $R_2$, $R_3$ and $R_4$ are the same or different and each is hydrogen or an acyl radical of a metabolite, or a pharmaceutically acceptable salt thereof.

(2) Cytidine or an acyl derivative of cytidine having the formula:

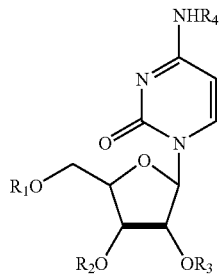

wherein $R_1$, $R_2$, $R_3$ and $R_4$ are the same or different and each is hydrogen or an acyl radical of a metabolite or a pharmaceutically acceptable salt thereof.

(3) An acyl derivative of uridine having the formula:

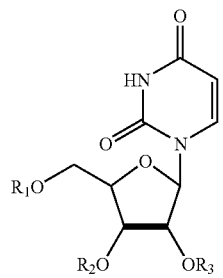

wherein $R_1$, $R_2$, and $R_3$ are the same, or different, and each is hydrogen or an acyl radical of
   a. an unbranched fatty acid with 5 to 22 carbon atoms,
   b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine,
   c. a dicarboxylic acid having 3–22 carbon atoms,
   d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(4) An acyl derivative of cytidine having the formula:

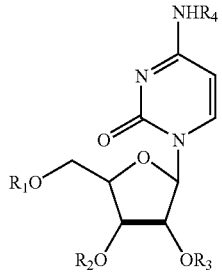

wherein $R_1$, $R_2$, $R_3$, and $R_4$ are the same, or different, and each is hydrogen or an acyl radical of
   a. an unbranched fatty acid with 5 to 22 carbon atoms,
   b. an amino acid selected from the group consisting of glycine, the L forms of phenylalanine, alanine, valine, leucine, isoleucine, tyrosine, proline, hydroxyproline, serine, threonine, cystine, cysteine, aspartic acid, glutamic acid, arginine, lysine, histidine carnitine and ornithine,
   c. a dicarboxylic acid having 3–22 carbon atoms,
   d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(5) An acyl derivative of uridine having the formula:

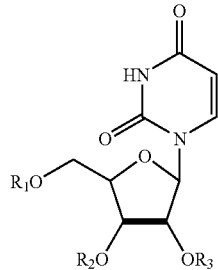

wherein at least one of $R_1$, $R_2$, or $R_3$ is a hydrocarbyloxycarbonyl moiety containing 2–26 carbon atoms and the remaining R substituents are independently a hydrocarbyloxycarbonyl or hydrocarbylcarbonyl moiety or H or phosphate.

(6) An acyl derivative of cytidine having the formula:

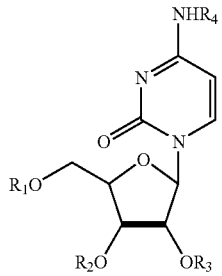

wherein at least one of $R_1$, $R_2$, $R_3$ or $R_4$ is a hydrocarbyloxycarbonyl moiety containing 2–26 carbon atoms and the remaining R substituents are independently a hydrocarbyloxycarbonyl or hydrocarbylcarbonyl moiety or H or phosphate.

(7) Orotic acid or salts thereof:

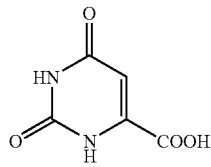

Pharmaceutically-acceptable salts of orotic acid include those in which the cationic component of the salt is sodium, potassium, a basic amino acid such as arginine or lysine, methylglucamine, choline, or any other substantially non-toxic water soluble cation with a molecular weight less than about 1000 daltons.

8) Alcohol-substituted orotate derivatives:

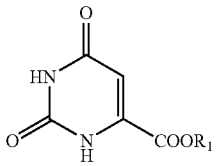

wherein $R_1$ is a radical of an alcohol containing 1 to 20 carbon atoms-joined to orotate via an ester linkage.

Also encompassed by the invention are the pharmaceutically acceptable salts of the above-noted compounds.

Advantageous compounds of the invention are short-chain (2 to 6 carbon atoms) fatty acid esters of uridine or cytidine. Particularly advantageous compounds are triacetyluridine, triacetylcytidine or salts of orotic acid.

Inhibitors of Uridine Phosphorylase

As an alternative or adjunct to the above-noted pyrimidine nucleotide precursors, the following compounds are useful in the invention. These agents elevate tissue uridine nucleotide levels by inhibiting catabolism of endogenous or exogenous uridine. Co-administration of uridine phosphorylase, inhibitors with pyrimidine nucleotide precursors reduces the amount of nucleotide precursor required to obtain therapeutic benefit.

Examples of inhibitors of uridine phosphorylase include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl]barbiturate, 5-benzyloxybenzylacetyl-1-[(1-hydroxy-2-ethoxy)methyl]barbiturate, and 5-methoxybenzylacetylacyclobarbiturate, 2,2'-anhydro-5-ethyluridine, and acyclouridine compounds, particularly 5-benzyl substituted acyclouridine congeners including but not limited to benzylacyclouridine, benzyloxy-benzylacyclouridine, aminomethyl-benzylacyclouridine, aminomethyl-benzyloxybenzylacyclouridine, hydroxymethyl-benzylacyclouridine, and hydroxymethyl-benzyloxybenzylacyclouridine. See also WO 89/09603 and WO 91/16315, hereby incorporated by reference.

DETAILED DESCRIPTION OF THE INVENTION

The subject invention relates to pyrimidine nucleotide precursors including acyl derivatives of cytidine, uridine, and orotate, and the use of these compounds and/or uridine phosphorylase inhibitors for treating or preventing pathological consequences of endotoxin and other inflammatory stimuli or mediators in animals, including humans.

The invention disclosed herein involves methods for enhancing the resistance of an animal to inflammatory stimuli and mediators. Examples presented below demonstrate both prophylaxis and treatment of toxicity due to endotoxin and other inflammatory stimuli. The method of the invention can be used in conjunction with other methods for treating or preventing sepsis or systemic inflammation.

A. Definitions

The term "pyrimidine nucleotide precursor" as used herein refers to a compound which is converted to a pyrimidine nucleotide following administration to an animal. This includes especially cytidine, uridine, or orotic acid, or prodrugs (including acyl derivatives) of these compounds.

The term "acyl derivative" as used herein means a derivative of a pyrimidine nucleoside in which a substantially nontoxic organic acyl substituent derived from a carboxylic acid is attached to one or more of the free hydroxyl groups of the ribose moiety of the oxypurine nucleoside with an ester linkage and/or where such a substituent is attached to the amine substituent on the purine ring of cytidine, with an amide linkage. Such acyl substituents are derived from carboxylic acids which include, but are not limited to, compounds selected from the group consisting of a fatty acid, an amino acid, nicotinic acid, dicarboxylic acids, lactic acid, p-aminobenzoic acid and orotic acid. Advantageous acyl substituents are compounds which are normally present in the body, either as dietary constituents or as intermediary metabolites.

The term "pharmaceutically acceptable salts" as used herein means salts with pharmaceutically acceptable acid addition salts of the derivatives, which include, but are not limited to, sulfuric, hydrochloric, or phosphoric acids.

The term "coadministered" means that at least two of the compounds of the invention are administered during a time frame wherein the respective periods of pharmacological activity overlap.

The term "amino acids" as used herein includes, but is not limited to, glycine, the L forms of alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids.

The term "fatty acids" as used herein means aliphatic carboxylic acids having 2–22 carbon atoms. Such fatty acids may be saturated, partially saturated or polyunsaturated.

The term "dicarboxylic acids" as used herein means fatty acids with a second carboxylic acid substituent.

The term "therapeutically effective amount" as used herein refers to that amount which provides therapeutic effects for a given condition and administration regimen.

The term "sepsis" as used herein is a systemic inflammatory disorder in which endogenous cytokines and other bioactive molecules, produced or released in response to an inflammatory stimulus such as bacterial endotoxin (a component of the cell wall of gram-negative bacteria), cause various symptoms including fever, neutropenia, blood coagulation disorders, hypotension, shock, and organ damage.

The term "inflammatory stimulus" as used herein means an exogenous agent which triggers an inflammatory response in an animal. Examples of inflammatory stimuli include bacteria, fungi, viruses, nonviable fragments or components of bacteria (such as endotoxin), fungi or viruses, or agents which trigger allergic or anaphylactic responses. In the case of autoimmune disorders, endogenous elements of a patient's tissues, e.g. particular cellular proteins function as inflammatory stimuli.

The term "mediator" as used herein means endogenous or exogenous (e.g. recombinant polypeptides) bioactive compounds, proteins, or polypeptides that typically mediate the biological effects of endotoxin or other inflammatory stimuli such as fungal polysaccharides. Examples of such agents include but are not limited to tumor necrosis factor (TNF), interleukin-1 (IL-1), interleukin-6 (IL-6), plasminogen activator inhibitor (PAI), leukotrienes, elements of the complement cascade, nitric oxide, or platelet-activating factor.

B. Compounds of the Invention

A primary feature of the present invention is the unexpected discovery that uridine and other pyrimidine nucleotide precursors do in fact protect otherwise normal animals (e.g. animal models in which the organism has not received a clinically-irrelevant hepatotoxic sensitizing agent like galactosamine or TCDD) from toxicity due to bacterial endotoxin and other inflammatory stimuli which produce tissue damage through elicitation of endogenous inflammatory mediators.

Tissue uridine nucleotide levels can be increased by administration of several precursors. Uridine and cytidine are incorporated into cellular nucleotide pools by phosphorylation at the 5' position; cytidine and uridine nucleotides are interconvertible through enzymatic amination and deamination reactions. Orotic acid is a key intermediate in de novo biosynthesis of pyrimidine nucleotides. Incorporation of orotic acid into nucleotide pools requires cellular phosphoribosyl pyrophosphate (PRPP). Alternatively (or in addition to provision of exogenous nucleotide precursors), availability of uridine to tissues is increased by administration of compounds which inhibit uridine phosphorylase, the first enzyme in the pathway for degradation of uridine. The compounds of the invention useful in enhancing resistance to endotoxin or inflammatory mediators include uridine, cytidine, orotate, prodrug forms of these pyrimidine nucleotide precursors, particularly acyl derivatives and phosphate esters, and inhibitors of the enzyme uridine phosphorylase. Compounds of the invention have the following structures:

In all cases except where indicated, letters and letters with subscripts symbolizing variable substituents in the chemical structures of the compounds of the invention are applicable only to the structure immediately preceding the description of the symbol.

(1) An acyl derivative of uridine having the formula:

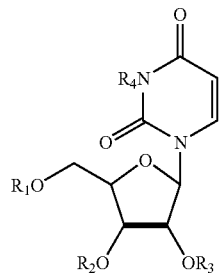

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

(2) An acyl derivative of cytidine having the formula:

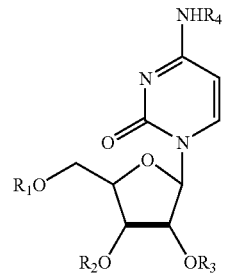

wherein $R_1$, $R_2$, $R_3$ and $R_4$ are the same or different and each is hydrogen or an acyl radical of a metabolite, provided that at least one of said R substituents is not hydrogen, or a pharmaceutically acceptable salt thereof.

The compounds of the invention useful in enhancing resistance to endotoxin include:

(3) An acyl derivative of uridine having the formula:

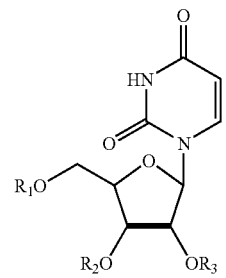

wherein $R_1$, $R_2$, and $R_3$ are the same, or different, and each is hydrogen or an acyl radical of a. an unbranched fatty acid with 5 to 22 carbon atoms, b. an amino acid selected from the group consisting of glycine, the L forms of alanine, valine, leucine, isoleucine, tyrosine, proline, hydroxyproline, serine, threonine, cystine, cysteine, aspartic acid, glutamic acid, arginine, lysine, histidine, carnitine and ornithine, c. a dicarboxylic acid having 3–22 carbon atoms, d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(4) An acyl derivatives of cytidine having the formula:

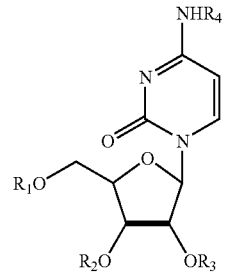

wherein $R_1$, $R_2$, $R_3$, and $R_4$ are the same, or different, and each is hydrogen or an acyl radical of a. an unbranched fatty acid with 5 to 22 carbon atoms, b. an amino acid selected from the group consisting of glycine, the L forms of phenylalanine, alanine, valine, leucine, isoleucine, tyrosine, proline, hydroxyproline, serine, threonine, cystine, cysteine, aspartic acid, glutamic acid, arginine, lysine, histidine carnitine and ornithine, c. a dicarboxylic acid having 3–22 carbon atoms, d. a carboxylic acid selected from one or more of the group consisting of glycolic acid, pyruvic acid, lactic acid, enolpyruvic acid, lipoic acid, pantothenic acid, acetoacetic acid, p-aminobenzoic acid, betahydroxybutyric acid, orotic acid, and creatine.

(5) An acyl derivative of uridine having the formula:

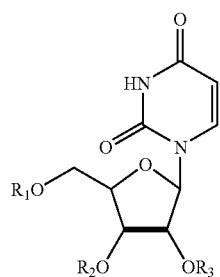

wherein at least one of $R_1$, $R_2$, or $R_3$ is a hydrocarbyloxycarbonyl moiety containing 2–26 carbon atoms and the remaining R substituents are independently a hydrocarbyloxycarbonyl or hydrocarbylcarbonyl moiety or H or phosphate.

(6) An acyl derivative of cytidine having the formula:

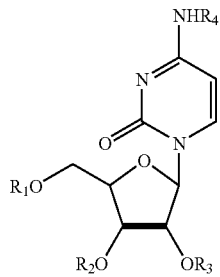

wherein at least one of $R_1$, $R_2$, $R_3$ or $R_4$ is a hydrocarbyloxycarbonyl moiety containing 2–26 carbon atoms and the remaining R substituents are independently a hydrocarbyloxycarbonyl or hydrocarbylcarbonyl moiety or H or phosphate.

(7) Orotic acid or salts thereof:

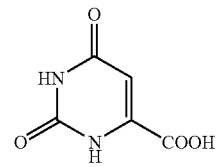

Pharmaceutically-acceptable salts of orotic acid include those in which the cationic component of the salt is sodium, potassium, a basic amino acid such as arginine or lysine, methylglucamine, choline, or any other substantially non-toxic water soluble cation with a molecular weight less than about 1000 daltons.

8) Alcohol-substituted orotate derivatives:

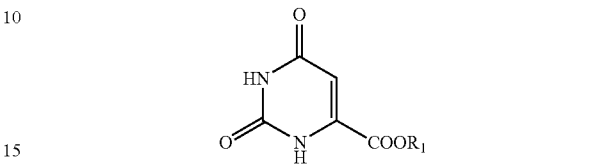

wherein $R_1$ is a radical of an alcohol containing 1 to 20 carbon atoms joined to orotate via an ester linkage.

Also encompassed by the invention are the pharmaceutically acceptable salts of the above-noted compounds.

Advantageous compounds of the invention are short-chain (2 to 6 carbon atoms) fatty acid esters of uridine or cytidine. Particularly advantageous compounds are triacetyluridine or triacetylcytidine.

Inhibitors of Uridine Phosphorylase

Examples of inhibitors of uridine phosphorylase include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl]barbiturate, 5-benzyloxybenzylacetyl-1-[(1-hydroxy-2-ethoxy)methyl]barbiturate, and 5-methoxybenzylacetylacyclobarbiturate, 2,2'-anhydro-5-ethyluridine, 5-ethyl-2-deoxyuridine and acyclouridine compounds, particularly 5-benzyl substituted acyclouridine congeners including but not limited to benzylacyclouridine, benzyloxybenzylacyclouridine, aminomethyl-benzylacyclouridine, aminomethylbenzyloxybenzyl-acyclouridine, hydroxymethyl-benzylacyclouridine, and hydroxymethylbenzyloxybenzylacyclouridine. See also WO 89/09603 and WO 91/16315, hereby incorporated by reference.

Compositions of the Invention

In one embodiment of the invention, novel pharmaceutical compositions comprise as an active agent one or more pyrimidine nucleotide precursors selected from the group comprised of uridine, cytidine or orotic acid or its salts, and acyl derivatives of these pyrimidine nucleotide precursors, together with a pharmaceutically acceptable carrier.

The compositions, depending on the intended use and route of administration, are manufactured in the form of a liquid, a suspension, a tablet, a capsule, a dragee, an injectable solution, or a suppository (see discussion of formulation below).

In another embodiment of the invention, the composition comprises at least one pyrimidine nucleotide precursor and an agent which inhibits the degradation of uridine, such as an inhibitor of the enzyme uridine phosphorylase. Examples of inhibitors of uridine phosphorylase include but are not limited to 5-benzyl barbiturate or 5-benzylidene barbiturate derivatives including 5-benzyl barbiturate, 5-benzyloxybenzyl barbiturate, 5-benzyloxybenzyl-1-[(1-hydroxy-2-ethoxy)methyl]barbiturate, 5-benzyloxybenzylacetyl-1-[(1-hydroxy-2-ethoxy)methyl]barbiturate, and 5-methoxybenzylacetyl-acyclobarbiturate, 2,2'-anhydro-5-ethyluridine, and acyclouridine compounds, particularly 5-benzyl substituted acyclouridine congeners including but not limited to benzylacyclouridine, benzyloxybenzylacyclouridine, aminomethyl-benzylacyclouridine, aminomethyl-benzyloxybenzyl-acyclouridine, hydroxymethyl-benzylacyclouridine, and hydroxymethyl-benzyloxybenzylacyclouridine. See also U.S. Pat. No. 5,077,280 and WO 91/16315, hereby incorporated by reference. Furthermore, it is within the scope of the invention to utilize an inhibitor of uridine phosphorylase alone, without coadministration of a pyrimidine nucleotide precursor, for the purpose of improving tissue resistance to endotoxin or inflammatory mediators.

In another embodiment, the compounds of the invention include in addition to one or more compounds of the invention, and at least one of the following compounds which are also useful for treating endotoxin toxicity or sepsis: Antibodies or other proteins which bind to endotoxin, TNF or IL-1; Polymyxin B conjugated to a polymeric support matrix (in order to reduce Polymyxin B toxicity while taking advantage of its capacity to bind and inactivate endotoxin); antagonists of IL-1 or TNF receptors; antibiotics; inhibitors of the arachidonic acid cascade; arginine or ornithine; corticosteroids; glucose; ATP; purine nucleotide precursors including inosine, adenosine, or acyl derivatives thereof; cyclic AMP or acyl derivatives thereof.

In another embodiment of the invention, the composition comprises at least one compound of the invention and an antibacterial, antifungal, or antiviral compound.

Therapeutic Uses of the Compounds and Compositions of the Invention

The compounds, compositions, and methods of the invention are useful to enhance resistance to endotoxin or other inflammatory stimuli or mediators in animals. The compounds include pyrimidine nucleotide precursors as well as compounds which inhibit enzymatic degradation of uridine.

The compounds and compositions of the invention are useful in treating mammals including humans; however, the invention is not intended to be so limited, it being within the contemplation of the invention to treat all animals that experience a beneficial effect from the administration of the active compounds of the invention.

A primary feature of the invention is the discovery that administration of uridine nucleotide precursors results in supra-normal resistance to toxic or lethal effects of endotoxin or other inflammatory stimuli or mediators in vivo.

The invention is furthermore embodied in the oral or systemic administration of a pharmaceutical compound or composition containing pyrimidine nucleotide precursors and/or agents which inhibit uridine catabolism, for the purpose of enhancing resistance to endotoxin, other inflammatory stimuli, or their mediators.

SIRS, Sepsis and Septic Shock

The compounds, compositions, and methods of the invention are useful for reducing tissue damage due to systemic inflammatory response syndrome (SIRS), including sepsis, triggered by bacterial (both gram-positive and gram-negative), viral, fungal, or parasitic (e.g. malaria) organisms. All of these types of infective organisms stimulate the formation or release of endogenous inflammatory mediators, resulting in tissue damage.

The compounds and compositions of the invention are administered to patients with symptoms of sepsis, e.g. fever, neutropenia, hypotension, etc., or prophylactically to patients at risk for sepsis, e.g. surgical patients, patients with serious burns or wounds, or patients with urinary tract catheters.

The compounds of the invention are optionally administered in conjunction with other agents which are useful in treating sepsis, including but not limited to one or more of the following: Antibodies or other proteins which bind to endotoxin, TNF or IL-1; Polymyxin B conjugated to a polymeric support matrix (in order to reduce Polymyxin B toxicity while taking advantage of its capacity to bind and inactivate endotoxin); antagonists of IL-1 or TNF receptors; antibiotics; inhibitors of the arachidonic acid cascade; leukotriene antagonists; arginine or ornithine; corticosteroids; glucose; ATP; inosine; cyclic AMP or acyl derivatives thereof. The compounds of the invention are administered either before, after, or during exposure of the animal or patient to one or more of these other agents.

For treatment or prevention of tissue damage due to sepsis, doses of the compounds of the invention ranging from about 0.5 to about 40 grams per day, advantageously 3 to 30 grams per day, are administered, depending on the therapeutic response and the condition of the patient. In patients with serious sepsis syndrome, the compounds of the invention are typically administered in liquid or suspension form via a nasogastric tube, especially if such a tube is already in place for delivery of nutrient suspensions or other enteral nutrition products. Patients with less serious illness typically receive compounds of the invention in either liquid form, or in capsules or tablets. Patients who do not tolerate oral administration of the compounds and compositions of the invention (e.g. patients on total parenteral nutrition due to gastrointestinal tract damage) receive compounds of the invention that are sufficiently water soluble, such as uridine itself, by intravenous infusion.

Following an episode of shock, trauma or sepsis, patients often enter into a persistent state of hypermetabolism which can lead to multiple organ failure, usually beginning with hepatic failure. The hypermetabolic phase is due to the influence of endotoxin and its mediators on metabolic regulation (Cerra et al., in *Molecular and Cellular Mechanisms of Septic Shock*, 265–277, Alan R. Liss, 1989). Hypermetabolism-organ failure is one of the leading causes of mortality among surgical intensive care patients. As demonstrated in the Examples, the compounds, compositions and methods of the invention are effective in reducing tissue damage and improving survival in animals subjected to endotoxin or other inducers of sepsis and organ failure. The compounds, compositions, and methods of the invention are useful in the treatment of patients at risk for hypermetabolic organ failure.

A serious consequence of sepsis is a propensity toward coagulation disorders, especially disseminated intravascular coagulation (DIC). In DIC, both blood coagulation and fibrinolysis are activated, so that blood clotting factors are rapidly consumed and aggregates of thrombin form in the circulation. DIC can result in either (or both) hemorrhage or thrombus formation. The liver is the primary site for synthesis of clotting factors and for clearing micro-aggregates of thrombin from the circulation. The protective and therapeutic effects of the compounds, compositions, and methods of the invention attenuate sepsis-induced alterations in blood coagulation (see Example 11).

Reduction of Toxicity of Therapeutic Cytokines

Many of the biological effects of endotoxin and other inflammatory stimuli are mediated by the release of endogenous bioactive molecules (mediators) from target cells, particularly macrophages and Kupffer cells (sessile macrophages in the liver). Evidence for this is that macrophages in the C3H/HEJ strain of mice are genetically non-responsive to endotoxin (in terms of releasing cytokines upon exposure to endotoxin), and endotoxin is relatively non-toxic in this strain. These mice are however sensitive to bioactive peptides normally released from macrophages, e.g. tumor necrosis factor (TNF), and toxicity of LPS is restored by transplantation of normal macrophages. TNF is generally held to be a primary mediator of endotoxin toxicity, but interleukin-1 (IL-1) and other agents also participate in the expression of endotoxin toxicity and sepsis.

Compounds, compositions, and methods of the invention are thus useful in modifying biological effects of inflammatory cytokines, whether produced endogenously (especially from macrophages), or introduced into the body from exogenous sources (e.g. polypeptides produced by recombinant DNA and fermentation technology).

Various inflammatory cytokines and even endotoxin itself have potential therapeutic applications. Tumor necrosis factor, as suggested by its name, can destroy tumors and synergizes with interferon-alpha in inhibiting viral infections. Thus, TNF, and even bacterial endotoxin itself (which elicits the release of endogenous TNF), have been administered to patients for the treatment of cancer. Classes of inflammatory cytokines with both therapeutic activity and toxicity which limits their clinical use include TNF, interleukins and interferons. The compounds, compositions and methods of the invention are useful in preventing or treating toxicity which occurs during therapeutic administration of such cytokines as well as inflammatory stimuli.

When endotoxin is administered to cancer patients by intravenous infusion, hepatic toxicity limits the dose of endotoxin which can be administered (Engelhardt R et al., *Cancer. Res.* 1991 51:2524–30). In non-hepatic cancers, protection of the liver from endotoxin permits administration of higher doses of endotoxin in order to maximize its antitumor efficacy. Endotoxin also has immunostimulant properties. The compounds of the invention are thus useful for improving the therapeutic index of endotoxin, endotoxin analogs or derivatives (e.g. Lipid A, Lipid X, Monophosphoryl Lipid A, etc.) or their mediators. Hepatic toxicity is also dose-limiting during intentional administration of TNF to humans (Kimura et al., *Cancer Chemother. Pharmacol.* 1987, 20:223–229). Inflammatory stimuli of yeast or fungal origin, such as the polysaccharides glucan or lentinan are also used therapeutically as immunomodulators for treatment of infections or cancer (Seljelid, *Scand. J. Immunol.* 1989, 29:181–92; Bowers et al., *J. Surg. Res.* 1989;47: 183–8). Double-stranded RNA, such polyinosine-polycytidine, also has therapeutic activity as an inflammatory stimulus for treatment of cancer or infections.

The inflammatory peptide Interleukin-1 (IL-1), which mediates some actions of endotoxin, similarly has important therapeutic potential (e.g. in restoring hematopoiesis after damage caused by cancer chemotherapy), but its use is limited by toxic side effects which may be attenuated by utilization of the compounds, compositions, and methods of the invention.

Interleukin-2 (IL-2) is used clinically for treatment of several varieties of cancer; it also has potential activity as an immunomodulator in treatment of various infections and in modulating the response to vaccines. Hepatic toxicity in response to IL-2 is not uncommon in patients receiving therapeutic doses of IL-2 for cancer treatment (Viens et al., *J. Immunother.* 1992 11:218–24). In an experimental model of autoimmune hepatitis induced by administration of concanavalin A to mice, hepatic damage is reported to be related to elevated production of endogenous IL-2 (Tiegs et al., *J. Clin. Invest.* 1992 90:196–203); as demonstrated in Example 10, compounds, compositions, and methods of the invention are effective in attenuating hepatic damage in this model. The compounds, compositions, and methods of the invention are useful in reducing side effects when administered in conjunction with IL-2; furthermore, the compounds, compositions, and methods of the inventions are useful in treating autoimmune hepatitis.

Interleukin 6, which has therapeutic potential in improving blood platelet production, induces hepatic TNF receptors, thus increasing tissue sensitivity to TNF. The compounds, compositions, and methods of the invention are thus useful for use in combination with IL-6 or similar agents which affect tissue senstivity to, or production of, TNF (Van Bladel et al., *Cytokine,* 1991 3:149–54).

The combination of a particular therapeutic cytokine and a pyrimidine nucleotide precursor and/or a uridine phosphorylase inhibitor is used for treatment of the disorders for which the particular therapeutic cytokine is known to be effective. For example, interleukin 2 is used for treatment of renal cancer, colon cancer, melanoma, leukemia and other neoplastic conditions. TNF has antitumor efficacy against a variety of cancer types, but its use in therapy has heretofore been limited by its toxicity, (Kimura et al., *Cancer. Chemother. Pharmacol.* 1987; 20:223–9). Endotoxin has shown significant antitumor efficacy (Engelhardt R et al., *Cancer. Res.* 1991 51:2524–30).

For prevention or treatment of toxicity due to administration of therapeutic cytokines, approximately 0.5 to 40 grams of a pyrimidine nucleotide precursor is administered daily for one to several days, depending on the duration of the cytokine treatment. The pyrimidine nucleotide precursors are administered before, during, or after administration of the therapeutic cytokine. The therapeutic cytokines are administered in the particular doses and regimens already established for experimental and clinical treatment of various forms of cancer, except that increased doses of cytokines may be tolerated when the pyrimidine nucleotide precursors of the invention are administered, as would be determined in simple dose-escalation studies for each cytokine or inflammatory stimulus.

Inflammatory Hepatitis: Liver Disorders Involving Endotoxin or Mediators

The liver is susceptible to damage by endotoxin or its mediators, particularly when liver function is impaired. Liver damage from many originating causes (e.g. choline deficiency, Reye's syndrome, or alcohol) which either increase hepatic sensitivity to endotoxin or inhibit endotoxin clearance, is in part mediated by bacterial endotoxin (normally present in the portal circulation due to leakage of small amounts from the intestine into the bloodstream) or mediators elicited by endotoxin (Nolan, *Gastroenterology,* 1975 69:1346–1356; Nolan, *Hepatology* 1989 10:887–91). Hepatic toxicity is dose-limiting in patients receiving intentional injections of endotoxin for possible efficacy in treating cancer (Engelhardt et al., *Cancer Research,* 1991 51:2524–2530).

As is demonstrated in the Examples below, the compounds, compositions, and methods of the invention significantly reduce hepatic damage induced by endotoxin and other inflammatory stimuli and mediators. The compounds, compositions, and methods of the invention are useful in treating, preventing, or attenuating liver damage in a large variety of conditions in which hepatoxicity due to endotoxin or other inflammatory stimuli or mediators are implicated in their etiology (whether or not systemic sepsis syndrome is present). Conditions in which damage to the liver by endotoxin or its mediators (e.g. TNF) are implicated include but are not limited to the following disease states:

A. Reye's Syndrome

Reye's syndrome is characterized by rapid hepatic failure and is most commonly found in children as a complication of influenza and other viral infections; aspirin may be a risk factor. The etiology of Reye's syndrome is believed to involve endotoxin or inflammatory mediators. Endotoxemia is found in most or all patients with Reye's syndrome; an animal model for Reye's syndrome involves treating rats with a combination of endotoxin and aspirin (Kilpatrick et al., *Metabolism,* 1989, 38:73–7).

B. Alcoholic Liver Damage

Excessive consumption of ethanol, in addition to problems associated with impaired mental and physical control associated with ethanol intoxication, is a significant cause of liver injury in humans. Endotoxin and TNF contribute to hepatic problems associated with exposure to alcohol. (Nolan J P, *Hepatology* 1989 10:887–91; Arai M, Nakano S, Okuno F, et al. *Hepatology* 1989; 9:846–851; McClain C J and Cohen D A, *Hepatology* 1989; 9:349–351).

C. Fulminant Hepatitis

Tumor necrosis factor is implicated in the etiology and progression of fulminant hepatitis, which can rapidly lead to hepatic failure and death (Aderka et al., *Med Hypotheses,* 1988 27:193–6)

D. Viral Hepatitis

Endotoxin contributes to hepatocyte damage occurring during viral hepatitis. Viral hepatitis reduces the $LD_{50}$ of endotoxin in animal models, and exclusion of endogenous endotoxin from experimental animals (by colectomy or by using axenic rodents) reduces the hepatic damage caused by a viral challenge. (Gut et al., *J. Infect. Disease.,* 1984, 149:621). In some cases of hepatitis, immune or inflammatory responses to hepatic viral infection mediated by T lymphocytes or macrophages contributes to liver damage. In either situation, the compounds, compositions, and methods of the invention are useful for treating hepatic damage related to viral infection. Example 14 demonstrates that the compounds and methods of the invention improve survival in an animal model of viral hepatitis.

Immunopathology contributes to liver injury in viral hepatitis in humans. Hepatitis B and C viruses do not necessarily directly injure cells. There is substantial evidence that immune responses to infected cells contributes significantly to liver injury. Activated cytotoxic T lymphocytes attack antigen-bearing infected cells, but also release cytokines like interferon-gamma which then recruit and activate inflammatory leukocytes in the liver and enhance hepatic sensitivity to macrophage activators like endotoxin (Ando et al., *J. Exp Med.* 178:1541–1554, 1993). In Examples 10 and 12, beneficial effects of compounds, compositions, and methods of the invention are presented in experimental models mimicking the key features of T Cell-mediated hepatic inflammatory injury with and without secondary exacerbation caused by endotoxin. These Examples support the utility of the compounds, compositions, and methods of the invention in viral hepatitis, as well as in autoimmune hepatitis and cell-mediated liver graft rejection.

E. Parasitic Infections

Hepatic damage and morbidity which occurs during malaria infection is mediated in part by TNF (Clark et al., *Am. J. Pathol.* 1987, 129:192–9).

F. Hepatic damage during total parenteral nutrition Hepatic complications are common in patients receiving total parenteral nutrition (TPN) and who have no underlying liver disease; exacerbation of pre-existing liver injury also occurs during TPN. Pappo et al. (*J. Surg. Res.,* 1991, 51:106–12) reported that endotoxin (LPS) derived from the overgrowth of intestinal gram-negative bacteria is responsible for TPN-associated hepatic steatosis, and that bowel decontamination and specific anti-LPS activity of polymyxin B will reduce fatty infiltration of the liver during TPN. Polymyxin B, which binds to and inactivates LPS, is toxic in humans, but served to demonstrate that hepatopathy observed during TPN is in fact mediated in part by endotoxin or TNF. Therefore, inclusion of effective amounts of compounds of the invention in TPN solutions is useful for reducing TPN-induced liver damage, as well as for treating underlying inflammatory liver injury. Compounds of the invention, especially uridine, cytidine, orotic acid, or water soluble salts and esters thereof, are either included in a TPN formulation or are administered separately but concurrently with TPN infusion. A typical TPN formula contains the basic nutrients needed to fulfill nutritional requirements in a form that is acceptable for intravenous administration. Thus, macromolecular dietary constituents like proteins or starches are provided in partially or fully digested form, e.g. as amino acids or sugars. A typical TPN formulation contains not only amino acids and sugars, but also other required nutrients like vitamins, minerals, and fats. Preferred doses of compounds of the invention to be used in conjunction with, or as constituents of, TPN formulas are in the range of 1 to 40 grams per day (usually in the range of 2 to 20 grams per day) either as a bolus injection or as a sustained infusion.

In the context of this embodiment of the invention, a patient need not be receiving all of his or her nutrient requirements by the parenteral route in order to obtain benefit from the compounds, compositions, and methods of the invention. However, this embodiment of the invention is particularly advantageous where patients are receiving 50% or more of their nutrient requirements by intravenous infusion.

Lead Poisoning

Lead poisoning can dramatically increase sensitivity to endotoxin. Lead-induced interference with hepatic metabolism is implicated in the effect of lead on endotoxin toxicity (Taki et al., *Eur. Surg. Res.,* 1985, 17:140–9).

H. Partial Hepatectomy

Following partial hepatectomy (e.g. for removal of cancerous tissue), morbidity and mortality from hepatic failure is not uncommon. Liver tissue undergoing regeneration after partial hepatectomy in animals is hypersensitive to the deleterious effects of endotoxin and mediators (Shirai et al., *Acta Pathol. Jpn.,* 1987, 37:1127–1134).

I. Postanesthetic Hepatitis

Inhalation anesthetics such as halothane can induce hepatitis, particularly if hepatic bloodflow is also impaired. Endotoxin is implicated in the etiology of postanesthetic hepatitis (Lomanto et al., *Anesth. Analg.,* 1972, 51:264–270); the compounds of the invention are thus useful for administration to patients (prophylactically, therapeutically, or both) undergoing inhalation anesthesia for preventing and treating hepatitis. Trauma itself may contribute to postanesthetic hepatitis. Trauma furthermore often induces translocation of bacteria and endotoxin from the gut into other tissues via the bloodstream. Surgery patients are among the groups most susceptible to endotoxin poisoning (due to infection). Therefore, treatment of surgical patients with pyrimidine nucleotide precursors (before, during, or after surgery) significantly improves their resistance to endotoxin poisoning.

J. Cholestatic Hepatitis

Hepatic injury due to bile duct obstruction or intrahepatic cholestasis is in part due to enterally-derived endotoxin. (Shibayama Y, 1989, *J. Pathol.* 159:335–9).

K. Liver Transplantation

In patients receiving liver transplants, the presence of high levels of endotoxin or inflammatory mediators preoperatively and at the end of the anhepatic period is associated with graft failure and a high mortality. Patients with primary nonfunction of their transplants typically have severe endotoxemia. Endotoxemia is implicated as a cause rather than an effect of perioperative complications and graft loss (Yokoyama et al, 1989, *Transplant Proc.* 21:3833–41). In a clinical situation, an animal, such as a human, receives a compound of the invention enterally or parenterally after a transplant, in doses ranging from about 1 to about 40 grams per day, though typically 2 to 20 grams, advantageously divided into one to about four doses or else administered as a continuous or intermittent enteral or parenteral infusion. A compound of the invention is also optionally incorporated into an enteral or parenteral nutrition formulation prior to administration. Patients often receive intravenous isotonic (5%) glucose for several days after liver transplantation as an alternative to more complete parenteral or enteral nutrition. A compound of the invention, especially uridine or cytidine, is advantageously formulated in an aqueous solution of 1 to 10% glucose. In a preferred embodiment, 1 to 40 grams per day, advantageously 2 to 20 grams, of a pyrimidine nucleotide precursor are administered per day. A secondary benefit of pyrimidine nucleotide precursors in liver disease or in recovery from a transplant is improved peripheral glucose utilization.

The donor liver can also be perfused with a solution containing a compound of the invention, advantageously uridine, cytidine, orotic acid or salts or acyl derivatives thereof, prior to or during implantation in the recipient. A pyrimidine nucleotide precursor, especially uridine, is included in a liver perfusion solution (also containing appropriate ions and other metabolites like glucose) at concentrations ranging from 10 micromolar to 10 millimolar.

Endotoxins and inflammatory mediators are also involved in other hepatic disorders; the diversity of the specific examples discussed above serve to indicate that the compounds, compositions, and methods of the invention are useful in treating or preventing a broad variety of liver diseases.

For treatment of inflammatory hepatitis, 0.5 to 40 grams (advantageously 3 to 30 grams) of a pyrimidine nucleotide precursor are administered daily, advantageously divided into one to about four doses. The duration of the treatment regimen depends on improvement of clinical symptoms; acute inflammatory liver disorders will typically require a shorter course of treatment than chronic degenerative conditions.

Other Disorders

As is demonstrated in Examples 2, 4–6, and 9, the compounds of the invention protect tissues other than liver, e.g. muscle, as indicated by serum creatine phosphokinase (CPK) levels in animals treated with endotoxin or the fungal inflammatory agent zymosan. Serum CPK activity is elevated as a consequence of damage to skeletal or heart muscle.

Cachexia, a syndrome of weight loss, tissue wasting and misutilization of nutrients is a common complication in patients with cancer. TNF and other inflammatory cytokines are implicated in the initiation and maintenance of cachectic states; "Cachectin" is a synonym for TNF. The compounds, compositions, and methods of the invention are useful for treating patients with cachexia.

Clearance of ethanol from the circulation is a process that is largely dependent on energy metabolism and redox balance in the liver, in addition to levels of the enzyme alcohol dehydrogenase. Example 13 demonstrates that compounds of the invention improve recovery from severe ethanol intoxication. The compounds and compositions of the invention are useful in reducing the severity of both the mental and physical impairment due to alcohol intoxication as well as longer-term health consequences of chronic alcohol ingestion such as liver injury. Compounds of the invention (e.g. triacetyluridine, uridine or cytidine) are administered orally before, during, or after ingestion of ethanol in doses of 0.5 to 40 grams per day, advantageously 1 to 20 grams.

Veterinary Applications

In horses and other large animals, there is a common syndrome known as laminitis, which is one consequence of endotoxin from the gut entering into the systemic circulation (often after the animal overeats carbohydrate-rich foods, changing the bacterial populations in the gut). The compounds, compositions, and methods of the invention, since they attenuate tissue damage due to endotoxin, are useful in treating or preventing laminitis and other effects of endotoxin poisoning in animals.

Administration and Formulation of Compounds and Compositions of the Invention

The compounds and compositions of the invention are administered orally, by parenteral injection, intravenously, or by other means, depending on the condition being treated and the status of the patient.

The compounds and compositions of the invention are administered chronically, intermittently, or acutely as needed. In the case of an event which involves endotoxin toxicity or systemic inflammatory syndrome, the compounds and compositions are administered prior to, during, or after such event.

The pharmacologically active compounds optionally are combined with suitable pharmaceutically acceptable carriers comprising excipients and auxiliaries which facilitate processing of the active compounds. These are administered as tablets, dragees, capsules, and suppositories. The compositions are administered for example orally, rectally, vaginally, or released through the buccal pouch of the mouth, and may be applied in solution form by injection, orally or by topical administration. The compositions may contain from about 0.1 to 99 percent, preferably from about 50 to 90 percent of the active compound(s), together with the excipient(s).

For parenteral administration by injection or intravenous infusion, the active compounds are suspended or dissolved in aqueous medium such as sterile water or saline solution. Injectable solutions or suspensions optionally contain a surfactant agent such as polyoxyethylenesorbitan esters, sorbitan esters, polyoxyethylene ethers, or solubilizing agents like propylene glycol or ethanol. The solution typically contains 1 to 25% of the active compounds. In one embodiment of the invention, the aqueous medium is a solution of 1 to 10% glucose in water or isotonic saline. In some circumstances concurrent intravenous adminisration of glucose and a compound of the invention, especially uridine, is advantageous. Uridine (and acyl derivatives of uridine) improve glucose peripheral glucose utilization, and insulin (which is generally released from the pancreas in response to glucose or other carbohydrates or some amino acids) enhances nucleoside uptake and utilization by cells.

For use in conjunction with parenteral nutrition, compounds of the invention are dissolved or suspended in parenteral nutrition products, either during manufacture of such products or shortly prior to their administration to patients. The concentration of pyridimine nucleotide precursor is adjusted in the parenteral nutrition formulation so that 1 to 40 grams, generally 2 to 20 grams, are delivered per day during infusion of the parenteral nutrition product. A typically parenteral nutrition formula contains and delivers nutritionally adequate portions of amino acids, carbohydrates, fats, vitamins, and minerals in sterile compositions suitable for intreavenous adminstration.

Suitable excipients include fillers such as sugars, for example lactose, sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch or potato starch, gelatin, tragacanth, methyl cellu-lose, hydroxypropylmethyl cellulose, sodium carboxymethyl cellulose and/or polyvinyl pyrrolidone.

Auxiliaries include flow-regulating agents and lubricants, for example, silica, talc, stearic acid or salts thereof, such as magnesium stearate or calcium stearate and/or polyethylene glycol. Dragee cores are provided with suitable coatings which, if desired, are resistant to gastric juices. For this purpose, concentrated sugar solutions are used, which optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate are used. Dyestuffs or pigments are optionally added to the tablets or dragee coatings, for example, for identification or in order to characterize different compound doses.

The pharmaceutical preparations of the present invention are manufactured in a manner which is itself known, for example, by means of conventional mixing, granulating, dragee-making, dissolving, or lyophilizing processes. Thus, pharmaceutical preparations for oral use are obtained by combining the active compound(s) with solid excipients, optionally grinding the resulting mixture and processing the mixture of granules, after adding suitable auxiliaries, if desired or necessary, to obtain tablets or dragee cores.

Other pharmaceutical preparations which are useful for oral delivery include push-fit capsules made of gelatin, as well as soft-sealed capsules made of gelatin and a plasticizer such as glycerol or sorbitol. The push-fit capsules contain the active compound(s) in the form of granules which optionally are mixed with fillers such as lactose, binders such as starches and/or lubricants such as talc or magnesium stearate, and, optionally stabilizers. In soft capsules, the active compounds are preferably dissolved or suspended in suitable liquids such as fatty oils, liquid paraffin, or polyethylene glycols. In addition, stabilizers optionally are added. Other formulations for oral administration include solutions, suspensions, or emulsions. In particular, a liquid form suitable for administration via an enteral catheter, e.g. a nasogastric tube, is advantageous, particularly for bedridden or unconscious patients.

Pharmaceutical preparations which are used rectally include, for example, suppositories which consist of a combination of active compounds with a suppository base. Suitable suppository bases are, for example, natural or synthetic triglycerides, paraffin hydrocarbons, polyethylene glycols or higher alkanols. In addition, gelatin rectal capsules which consist of a combination of the active compounds with a base are useful. Base materials include, for example, liquid triglycerides, polyethylene glycols, or paraffin hydrocarbons.

Suitable formulations for parenteral administration include aqueous solutions of the active compounds in water soluble form, for example, water soluble salts. In addition, suspensions of the active compounds as appropriate in oily injection suspensions are administered. Suitable lipophilic solvents or vehicles include fatty oils, for example, sesame oil, or synthetic fatty acid esters, for example, ethyl oleate or tri-glycerides. Aqueous injection suspensions optionally include substances which increase the viscosity of the suspension which include, for example, sodium carboxymethylcellulose, sorbitol and/or dextran. The suspension optionally contains stabilizers.

Synthesis of the Compounds of the Invention

Acylated derivatives of pyrimidine nucleosides are synthesized by reacting a pyrimidine nucleoside or congener with an activated carboxylic acid. An activated carboxylic acid is one that has been treated with appropriate reagents to render its carboxylate carbon more susceptible to nucleophilic attack than is the case in the original carboxylic acid. Examples of useful activated carboxylic acids for synthesis of the compounds of the invention are acid chlorides, acid anhydrides, n-hydroxysuccinimide esters, or carboxylic acids activated with BOP-DC. Carboxylic acids may also be linked to pyrimidine nucleosides or congeners with coupling reagents like dicyclohexylcarbodiimide (DCC).

During preparation of the acyl compounds of the invention, when the acid source of the desired acyl derivative has groups which interfere with the acylation reactions, e.g., hydroxyl or amino groups, these groups are blocked with protecting groups, e.g., t-butyldimethylsilyl ethers or t-BOC groups, respectively, before preparation of the anhydride. For example, lactic acid is converted to 2-t-butyldimethylsiloxypropionic acid with t-butyldimethylchlorosilane, followed by hydrolysis of the resulting silyl ester with aqueous base. The anhydride is formed by reacting the protected acid with DCC. With amino acids, the N-t-BOC derivative is prepared, using standard techniques, which is then converted to the anhydride with DCC. With acids containing more than one carboxylate group (e.g., succinic, fumaric, or adipic acid) the acid anhydride of the desired dicarboxylic acid is reacted with a pyrimidine nucleoside in pyridine or pyridine plus dimethylformamide or dimethylacetamide.

Amino acids are coupled to the exocyclic amino groups of cytidine, and to hydroxyl groups on the aldose moiety of pyrimidine nucleosides or their congeners, by standard methods using DCC in a suitable solvent, particularly a mixture of (i) methylene chloride and (ii) dimethylacetamide or dimethylformamide.

Carbyloxycarbonyl derivatives of non-methylated pyrimidine nucleosides are prepared by reacting the nucleoside with the appropriate carbylchloroformate in a solvent such as pyridine or pyridine plus dimethylformamide under anhydrous conditions. The solvent is removed under vacuum, and the residue is purified by column chromatography.

It will be obvious to the person skilled in the art that other methods of synthesis can be used to prepare the compounds of the invention.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLES

Example 1

Triacetyluridine and Uridine Improve Survival in Mice Treated with Killed E. Coli Purpose:

Sepsis syndrome can be initiated by gram-negative bacteria even if they are not alive, since the primary trigger is endotoxin, a component of the bacterial cell wall. The purpose of this study was to determine the effect of oral triacetyluridine and parenteral uridine on survival of mice treated with a lethal dose of killed E. Coli bacteria Methods:

Eighteen female Balb/C mice (eight weeks old) were divided into groups of six animals each. All mice received 500 micrograms of an acetone powder of E. Coli (serotype 0111:B4) suspended by sonication in 0.2 ml of saline. Mice in one group received uridine (2000 mg/kg in 0.2 ml saline) by i.p. injection two hours prior to administration of the E. Coli. Another group of mice received triacetyluridine (6000 mg/kg in a vehicle of 1:1 corn oil/water containing 2.5% Tween 80) by oral intubation. Survival was monitored for one week.

A. n=6 E. Coli (Control)
B. n=6 E. Coli (Control)+Urd i.p.
C. n=6 E. Coli (Control)+TAU p.o.

Results:

Animals in the Control group appeared to be in shock and were hypothermic 18 hours after administration of the E. Coli powder. Animals in the treated groups were active and maintaining body temperature, although their coats were scruffy throughout the first 48 hours of the observation period. Animals surviving 48 hours recovered completely. All of the mice treated only with E. Coli died within 48 hours. All mice treated with either uridine or triacetyluridine survived administration of killed E. Coli.

Example 2

Dose-Response Study of Uridine in Protection of Tissues from Endotoxin Damage

Purpose:

The purpose of this study was to determine the dose-response characteristics for uridine in prevention of inflammatory tissue damage caused by endotoxin (LPS).

Methods:

Female Balb/C mice (eight weeks old) were divided into six groups of six animals each. One group of animals remained untreated to provide basal values for serum chemistry indices of tissue damage. Mice in the remaining five groups received 100 micrograms of *Salmonella Typhimurium* endotoxin by i.p. injection in a volume 0.2 ml saline. Two hours prior to endotoxin administration, the five groups of mice received uridine in doses of 0, 500, 1000, 2000 and 4000 mg/kg i.p. (in 0.2 ml saline) respectively. Eighteen hours after endotoxin administration, blood samples were collected for determination of serum chemistry values of indicators of tissue damage.

Results:

Uridine produced a dose-dependent protection of tissues against damage from endotoxin administration. ALT, AST, and SDH are specific indicators of liver damage; CPK is an indicator of damage to muscle; LDH is released from both liver and muscle. The most effective uridine dose in mice in this experiment was 2000 mg/kg.

TABLE 1

Uridine attenuates endotoxin-induced tissue damage

| | ALT | AST | LDH | CPK | SDH |
|---|---|---|---|---|---|
| Basal (No LPS) | 198 ± 124 | 137 ± 26 | 708 ± 177 | 906 ± 211 | 49 ± 2 |
| Control (LPS) | 3768 ± 482 | 4176 ± 459 | 8406 ± 850 | 11628 ± 2398 | 1170 ± 157 |
| Uridine 500 | 2568 ± 678 | 3090 ± 871 | 5988 ± 1225 | 8832 ± 1089 | 834 ± 192 |
| Uridine 1000 | 1338 ± 401* | 1206 ± 314* | 3101 ± 860* | 4431 ± 1529* | 404 ± 95* |
| Uridine 2000 | 605 ± 236* | 620 ± 174* | 1990 ± 642* | 4531 ± 2139* | 125 ± 45* |
| Uridine 4000 | 1120 ± 970* | 744 ± 457* | 3441 ± 2378* | 8680 ± 6746* | 135 ± 75* |

*= Different from Control (LPS i.p.), $P < .02$
ALT = Alanine Aminotransferase
AST = Aspartate Aminotransferase
LDH = Lactate Dehydrogenase
CPK = Creatine Phosphokinase
SDH = Sorbitol Dehydrogenase

Example 3

Oral Triacetyluridine Improves Survival of Mice Treated with a Lethal Dose of *Salmonella Typhimurium* Endotoxin Purpose:

Sepsis syndrome caused by gram-negative bacteria is mediated primarily through endotoxin, a lipopolysaccharide constituent of the bacterial wall. The purpose of this experiment was to determine the effect of an orally-administered uridine prodrug (Triacetyluridine; TAU) on survival of mice treated with a lethal dose of purified *Salmonella Typhimurium* endotoxin (LPS).

Methods:

Twenty female Balb/C mice (eight weeks old) were divided into two groups of ten animals each. All mice received 100 micrograms of *Salmonella Typhimurium* endotoxin by intraperitoneal injection in 0.2 ml of saline. One group of mice received triacetyluridine (6000 mg/kg in a vehicle of 1:1 corn oil/water containing 2.5% Tween 80) by oral intubation. Survival was monitored for one week.

Results:

All ten of the animals which received endotoxin alone died within 48 hours. Nine of the ten mice that received oral TAU survived for the seven day observation period and appeared to have recovered completely.

Example 4

Oral Triacetyluridine Reduces Tissue Damage Caused by Endotoxin

Purpose:

Bacterial endotoxin causes damage to the liver and other organs which can be assessed and quantified by determining serum levels of enzymes and other markers of tissue integrity and function. The purpose of this study was to determine the dose-response characteristics of orally-administered triacetyl uridine (TAU) in attenuating tissue damage due to endotoxin.

Methods:

Female Balb/C mice (eight weeks old) were divided into groups of five animals each. One group of animals remained untreated to provide basal values for serum chemistry indices of tissue damage. Mice in the other four groups received 100 micrograms of *Salmonella Typhimurium* endotoxin by i.p. injection, in a volume 0.2 ml saline. Three groups of endotoxin-treated mice also received TAU 2 hours before endotoxin in doses of 2000, 4000, and 6000 mg/kg by oral intubation in a volume of 0.4 ml. The TAU was formulated as a suspension in 1% carboxymethylcellulose in water. The remaining group (Controls) received the carboxymethylcellulose vehicle by oral intubation.

Results:

Oral TAU administration reduced the levels of serum chemistry indicators of tissue damage. The beneficial effect on prevention of endotoxin-induced organ damage was dose dependent.

TABLE 2

TAU attenuates endotoxin-induced tissue damage

| | ALT | AST | LDH | SDH |
|---|---|---|---|---|
| Basal (No LPS) | 130 ± 46 | 148 ± 32 | 563 ± 132 | 41 ± 5 |
| Control (LPS) | 3679 ± 703 | 4798 ± 927 | 6998 ± 1064 | 1128 ± 174 |
| TAU 2000 | 2632 ± 915 | 3151 ± 1085 | 5419 ± 1561 | 793 ± 294 |
| TAU 4000 | 1463 ± 382* | 1940 ± 456* | 3878 ± 672* | 345 ± 106* |
| TAU 6000 | 365 ± 91* | 403 ± 61* | 1221 ± 181* | 104 ± 18* |

*= Different from Control (LPS i.p. + vehicle p.o.), P < .02
ALT = Alanine Aminotransferase
AST = Aspartate Aminotransferase
LDH = Lactate Dehydrogenase
CPK = Creatine Phosphokinase
SDH = Sorbitol Dehydrogenase

Example 5

Uridine Reduces Tissue Damage in Mice Treated with Carrageenan as a Potentiator of Endotoxin Toxicity Carrageenan is a polysaccharide derived from seaweed which modifies the activity of macrophages, which are principal cellular mediators of systemic inflammatory response to endotoxin. Macrophages release inflammatory peptides and other compounds in response to endotoxin. Carrageenan pretreatment sensitizes macrophages so that much less endotoxin than normal is required to elicit a serious systemic inflammatory response. Furthermore, a somewhat different spectrum of inflammatory mediators is involved in the toxic effects of the combination of carrageenan plus endotoxin compared to endotoxin alone (Franks et al., *Infection and Immunity*, 59: 2609–2614 [1991]). The purpose of this experiment was to determine the effect of uridine on tissue damage induced by a combination of carrageenan and endotoxin.

Methods:

Female Balb/C mice (eight weeks old) were divided into five groups of six animals each. One group of animals remained untreated to provide basal values for serum chemistry indices of tissue damage. Mice in the other four groups received 2 mg of lambda carrageenan in 0.2 ml saline by i.p. injection; three of these groups also received, one hour later, 2 micrograms of *Salmonella Typhimurium* endotoxin, also by i.p. injection in a volume 0.2 ml saline. Two of the groups that received both carrageenan and endotoxin also received uridine (2000 mg/kg i.p. in 0.2 ml saline); one group was treated with uridine 30 minutes after administration of endotoxin, and the other received 3 uridine pretreatments, 24, 6, and 2 hours before endotoxin administration, at 2000 mg/kg/dose i.p. Eighteen hours after endotoxin administration, blood samples were collected for determination of serum chemistry values of indicators of tissue damage.

Results:

The combination of carrageenan with a low dose of endotoxin (2 mg) resulted in significant tissue damage as evaluated by serum chemistry indices. Treatment with uridine either before or after administration of endotoxin resulted in significant attenuation of tissue damage due to the carrageenan-endotoxin combination. Data are shown below.

TABLE 3

Uridine attenuates endotoxin-induced tissue damage in carrageenan-sensitized mice

|  | ALT | AST | LDH | CPK | SDH |
|---|---|---|---|---|---|
| Basal (No LPS) | 223 ± 77 | 141 ± 35 | 700 ± 145 | 747 ± 278 | 33 ± 1 |
| Control (LPS) | 1937 ± 235 | 2072 ± 149 | 7360 ± 354 | 11612 ± 1513 | 107 ± 17 |
| Uridine | 817 ± 202* | 989 ± 139* | 4385 ± 454* | 5485 ± 1638* | 80 ± 12* |
| Uridine (posttreatment) | 770 ± 141* | 891 ± 79* | 4416 ± 283* | 5033 ± 565* | 117 ± 9 |

*= Different from Control, P < .05
ALT = Alanine Aminotransferase
AST = Aspartate Aminotransferase
LDH = Lactate Dehydrogenase
CPK = Creatine Phosphokinase
SDH = Sorbitol Dehydrogenase Example 6

Uridine Improves Survival in Zymosan-Treated Mice

Purpose:

Zymosan is a yeast component, primarily polysaccharide, which induces systemic inflammation and activation of complement. In fungal infections in general (including but not limited to yeast infections), such polysaccharides participate in the induction of a sepsis response. Zymosan administration to rodents is considered to be a suitable model for multiple organ failure syndrome (Goris et al. (1986) *Arch. Surg.* 121:897–901; Steinberg et al. (1989) *Arch. Surg.* 124:1390–1395). Mortality at minimum lethal doses of zymosan is due in part to gut damage leading to translocation of bacteria and bacterial toxins from the gut into the bloodstream (Deitch et al., (1992) *J. Trauma* 32:141–147).

Methods:

Female Balb/C mice (eight weeks old) were divided into groups of five animals each:
1. Zymosan 15 mg
2. Zymosan 15 mg+Uridine
3. Zymosan 20 mg
4. Zymosan 20 mg+Uridine
5. Basal Zymosan A was suspended in mineral oil at a concentration of 50 mg/ml and administered by intraperitoneal injection. Uridine (2000 mg/kg) was administered by intraperitoneal injection in a volume of 0.2 ml two hours before administration of Zymosan.

18 hours after administration of Zymosan, blood samples were collected from both groups of mice that received 20 mg Zymosan and from a basal (untreated) group for subsequent measurement of serum chemistry indices of tissue damage.

Results:

| Group | Survival |
|---|---|
| A. Survival at 48 hours: | |
| Zymosan 15 mg/kg | 0/5 |
| Zymosan 15 mg/kg + Uridine | 5/5 |
| Zymosan 20 mg/kg | 0/5 |
| Zymosan 20 mg/kg + Uridine | 3/5 |
| B. Survival at 14 days (complete recovery) | |
| Zymosan 15 mg/kg | 0/5 |
| Zymosan 15 mg/kg + Uridine | 4/5 |

Uridine significantly improved survival time and incidence of long-term survivors among mice treated with Zymosan.

C. Serum Chemistry Indices of Tissue Damage

TABLE 4

Uridine attenuates Zymosan-induced tissue damage

|  | ALT | AST | LDH | CPK | SDH |
|---|---|---|---|---|---|
| Basal | 50 ± 22 | 93 ± 41 | 899 ± 198 | 532 ± 731 | 52 ± 25 |
| Zymosan | 397 ± 140 | 392 ± 97 | 1974 ± 392 | 2107 ± 1172 | 81 ± 15 |
| Zymosan + Uridine | 120 ± 126 | 273 ± 131 | 1419 ± 244 | 754 ± 370 | 58 ± 22 |

ALT = Alanine Aminotransferase
AST = Aspartate Aminotransferase
LDH = Lactate Dehydrogenase
CPK = Creatine Phosphokinase
SDH = Sorbitol Dehydrogenase Example 7

Comparison of Effects of Uridine Versus Arginine on Survival of Endotoxin-Treated Mice Purpose:

The amino acid arginine is reported to have beneficial effects in sepsis syndrome (Leon et al. *J. Parenteral and Enteral Nutrition,* 1991, 15:503–508). The purpose of this study was to compare the efficacy of uridine with that of arginine, an agent which supports liver function in sepsis syndrome and which is clinical use for this purpose.

Methods:

Female Balb/C mice weighing 25 grams were divided into five groups of five or six animals each. Mice in the remaining five groups received 125 micrograms of *Salmonella Typhimurium* endotoxin (LPS) by i.p. injection in a volume 0.2 ml saline. Two hours prior to endotoxin administration, the five groups of mice received injections of:

1) Saline (Controls)
2) Uridine 2000 mg/kg
3) Arginine 25 mg/kg
4) Arginine 250 mg/kg
5) Arginine 1250 mg/kg All drugs were administered i.p. in 0.2 ml saline. The numbers of surviving mice in each group were determined 16, 20, and 24 hours.

Results:

Only one of the Control animals was alive 16 hours after LPS; in contrast, the majority of the animals treated with uridine or arginine were alive at this point. However, by 24 hours after administration of endotoxin, the only surviving animals were in the group treated with uridine. All three doses of arginine did improve survival time (but did not produce any long-term survivors), and the lowest dose (25 mg/kg) was more effective than the highest dose (1250 mg/kg). Uridine was clearly more effective than arginine in promoting survival of endotoxin-treated animals.

TABLE 5

Effect of uridine vs arginine on survival after LPS administration

| | Time after LPS (hr) | | |
|---|---|---|---|
| Groups | 16 | 20 | 24 |
| 1. Control | 1/6 | 0/6 | 0/6 |
| 2. Uridine | 5/5 | 5/5 | 5/5 |
| 3. Arg 25 | 5/5 | 3/5 | 0/5 |
| 4. Arg 250 | 4/5 | 2/5 | 0/5 |
| 5. Arg 1250 | 4/6 | 1/6 | 0/6 |

Example 8

Orotic Acid Improves Survival of Mice Treated with Salmonella Typhimurium Endotoxin Purpose:

Sepsis syndrome caused by gram-negative bacteria is mediated primarily through endotoxin, a lipopolysaccharide constituent of the bacterial wall. The purpose of this experiment was to determine the effect of orotate on survival of mice treated with a lethal dose of purified Salmonella Typhimurium endotoxin.

Methods:

Twenty female Balb/C mice (eight weeks old) were divided into two groups of ten animals each. One group of mice received four treatments with lysine orotate (200 mg/kg/dose; 9 AM and 2 PM on each of two consecutive days). Lysine orotate is a water-soluble salt of orotic acid; lysine alone does not improve survival of endotoxin-treated mice. Control animals received 0.2 ml of sterile water on the same treatment schedule. All mice received 100 micrograms of Salmonella Typhimurium endotoxin (LPS) by intraperitoneal injection in 0.2 ml of saline immediately after the last dose of lysine orotate. Survival was monitored for one week.

Results:

All of the mice in the Control group died within 48 hours. Nine of the ten mice treated with Lysine Orotate survived the full 72 hour observation period and were still alive and appeared to recover completely one week after LPS administration.

TABLE 6

Orotate improves survival of endotoxin-treated mice

| | Survival after endotoxin treatment | | | | | |
|---|---|---|---|---|---|---|
| Time (hr after LPS) | 24 | 26 | 28 | 32 | 48 | 72 |
| Control | 6/10 | 4/10 | 3/10 | 2/10 | 0/10 | 0/10 |
| LOR | 10/10 | 10/10 | 10/10 | 10/10 | 9/10 | 9/10 |

Example 9

Orotic Acid Protects Tissues Against Endotoxin Damage

Purpose:

The purpose of this study was to demonstrate the protective effect of orotic acid in prevention of inflammatory tissue damage caused by endotoxin.

Methods:

Female Balb/C mice (eight weeks old) were divided into three groups of six animals each. One group of animals remained untreated to provide basal values for serum chemistry indices of tissue damage. Mice in the remaining two groups received 100 micrograms of Salmonella Typhimurium endotoxin (LPS) by i.p. injection in a volume 0.2 ml saline. Two hours prior to endotoxin administration, mice in one group received lysine orotate in a dose corresponding to 100 mg/kg of free orotic acid. Eighteen hours after endotoxin administration, blood samples were collected for determination of serum chemistry content of indicators of tissue damage.

Results:

Orotate protected tissues against damage from endotoxin administration.

TABLE 7

Orotate attenuates endotoxin-induced tissue damage

| | ALT | AST | LDH | CPK | SDH |
|---|---|---|---|---|---|
| Basal (No LPS) | 132 ± 14 | 165 ± 21 | 681 ± 552 | 1258 ± 233 | 42 ± 1 |
| Control (LPS) | 2827 ± 413 | 2860 ± 506 | 6833 ± 1167 | 6820 ± 365 | 680 ± 142 |
| Orotate + LPS | 252 ± 99* | 415 ± 77* | 1641 ± 274* | 1040 ± 283* | 89 ± 7* |

*= Different from Control (LPS i.p.), P < .02
ALT = Alanine Aminotransferase
AST = Aspartate Aminotransferase
LDH = Lactate Dehydrogenase
CPK = Creatine Phosphokinase
SDH = Sorbitol Dehydrogenase

Example 10

Uridine and Triacetyluridine Attenuate Hepatic Damage Caused by Concanavalin A Purpose:

Interleukin-2 (IL-2) is used clinically for treatment of several varieties of cancer. Hepatic toxicity in response to IL-2, is not uncommon in patients receiving therapeutic doses of IL-2 for cancer treatment (Viens et al., *J. Immunother.* 1992 11:218–24). In an experimental model of autoimmune hepatitis induced by administration of Concanavalin A (Con A) to mice, hepatic damage is reported to be related to elevated production of endogenous IL-2 (Tiegs et al., *J. Clin. Invest.* 1992 90:196–203). The purpose of this study was to demonstrate the utility of the compounds and methods of the invention in attenuating hepatic damage initiated by administration of Con A.

Methods:

Female Balb/C mice (eight weeks old) were divided into four groups of five animals each. One group of animals remained untreated to provide basal values for serum chemistry indices of tissue damage. Mice in the remaining three groups received 10 mg/kg Concanavalin A by intravenous (tail vein) injection in a volume of 0.2 ml saline. Two hours prior to receiving Con A, one of these groups of mice received uridine (2000 mg/kg i.p. in 0.2 ml saline) and another group received triacetyluridine (6000 mg/kg orally, in 0.6 ml of a 1:1 corn oil/water emulsion containing 2.5% Tween 80); the remaining Con A-treated group (Control) received 0.2 ml saline i.p. two hours prior to Con A. Twenty hours after administration of Con A, blood samples were collected from all mice for determination of serum levels of various indices of tissue damage or metabolic dysfunction.

Results:

Con A administration resulted in significant damage to the liver, as assessed by serum levels of the enzymes ALT, AST, and SDH. Con A did not signficantly elevate levels of creatine phosphokinase (CK), an enzyme found primarily in muscle; tissue damage due to Con A in this model is more specifically localized in the liver than is damage due to endotoxin. Uridine and TAU both reduced the liver damage produced by Con A administration, as shown in Table 8 below.

Liver damage in the Con A model used in this study is related to elevated IL-2 levels, and is mediated through T lymphocytes. Therefore, the compounds and methods of the invention are useful in reducing side effects due to therapeutic administration of IL-2; furthermore, the compounds and methods of the inventions are useful in treating autoimmune hepatitis.

Example 11

Uridine Attenuates Sepsis Induced Alterations in Blood Coagulation

Purpose:

Disseminated Intravascular Coagulation (DIC) is a serious consequence of sepsis, in which both blood coagulation and fibrinolysis are activated, so that blood clotting factors are rapidly consumed. DIC can result in hemorrhage or thrombus formation. The liver is the primary site for synthesis of clotting factors and for clearing micro-aggregates of thrombin from the circulation. This purpose of this experiment was to determine the effect of pyrimidine nucleotide precursors on coagulation disorders induced by sepsis. Partial thromboplastin time was used as an index of the status of the blood coagulation system.

Methods:

Thirty female Balb/C mice (eight weeks old) were divided into three groups of ten animals each. One group of mice remained untreated, and was used to determine basal values for partial thromboplastin time. Two groups of mice received received 30 mg/kg killed *E. Coli* (strain 0111:B4); Two hours before *E. Coli* administration, one group received uridine (2000 mg/kg) by intraperitoneal injection. 20 hours after *E. Coli* administration, plasma samples were collected from all thirty mice for determination of partial thromboplastin time (PTT). 0.27 ml of blood was collected via the retro-orbital plexus into a tube containing 0.03 ml of 3.5% sodium citrate, pH 4. Plasma was separated by centrifugation, and 100 microliters of plasma was transferred to a clean 1.5 ml Eppendorf tube for determination of PTT with a commercial kit.

Results:

Administration of killed *E. Coli* resulted in a prolongation of the normal partial thromboplastin time. Uridine attenuated the sepsis-induced change in coagulation time, as shown in Table 9.

TABLE 8

Uridine and Triacetyluridine attenuate liver damage caused by Concanavalin A

|  | ALT | AST | LDH | CPK | SDH |
| --- | --- | --- | --- | --- | --- |
| Basal (No Con A) | 144 ± 18 | 217 ± 27 | 790 ± 90 | 2392 ± 370 | 51 ± 2 |
| Con A | 2652 ± 847 | 2765 ± 1030 | 4335 ± 1385 | 2572 ± 486 | 1114 ± 318 |
| Con A + Uridine | 289 ± 115* | 394 ± 114* | 973 ± 202* | 1996 ± 317 | 163 ± 68* |
| Con A + TAU | 575 ± 286* | 613 ± 221 | 1380 ± 270 | 1951 ± 435 | 283 ± 143* |

*= Different from Control (LPS i.p.), P < .02
ALT = Alanine Aminotransferase
AST = Aspartate Aminotransferase
LDH = Lactate Dehydrogenase
CPK = Creatine Phosphokinase
SDH = Sorbitol Dehydrogenase Table 9: Uridine attenuates sepsis-induced alterations in partial thromboplastin time

| Partial Thromboplastin Time | |
|---|---|
| Group | PTT (seconds) |
| Basal (Normal) | 32.3 ± 1.3 |
| E. Coli | 69.8 ± 5.4 |
| E. Coli + Uridine | 51.2 ± 2.1* |

*= different from control (E. Coli alone) value, P < .05

Example 12

Combined Liver Injury Due to T Cells and Endotoxin

Several important forms of viral hepatitis as well as autoimmune hepatitis are initiated by cytotoxic T cells which attack hepatocytes bearing appropriate viral or other antigens. Since endotoxin participates in liver damage initiated by a number of other agents like carbon tetrachloride, choline deficiency, ethanol, or cholestasis, studies were conducted to determine whether liver injury caused by T cells induces hepatic hypersensitivity to endotoxin. Following this experiment, the effect of TAU on combined liver injury due to both T lymphocytes and endotoxin was investigated.

Example 12A

Concanavalin A Potentiates Endotoxin-Induced Tissue Damage

Groups (n=6) of female Balb/C mice, age eight weeks, received, Concanavalin A (2.5 mg/kg i.v.), endotoxin (*Salmonella Typhimurium*, 0.5 mg/kg), or a combination of Con A and endotoxin. The Con A was administered twenty four hours before endotoxin. Blood samples were taken 18 hours after injection of endotoxin (or its vehicle in the groups of mice that did not receive endotoxin). The "Basal" group of mice received vehicle only (saline) instead of Con A or endotoxin.

SDH are markers for liver damage; CPK is an indicator for muscle damage). However, in mice treated with the combination of Con A and endotoxin, significantly greater damage was observed. The toxicity of Con A in this model is believed to be specifically related to T Lymphocyte-mediated liver damage (Tiegs et al., *J. Clin. Invest.* 90:196–203, 1992). Therefore, these results support the view that enterally-derived endotoxin participates in liver damage attributed to cytotoxic T lymphocytes (i.e. in viral and autoimmune hepatitis), as has been demonstrated for liver damage initiated by other primary insults including carbon tetrachloride, choline deficiency, D-galactosamine, and viral infections.

Example 12B

TAU Attenuates Combined Liver Injury Due to CTL's and Endotoxin

Experimental hepatitis initiated by intravenous administration of concanavalin A (Con A) is mediated by activation of cytoxic T lymphocytes. Liver injury in this model results in a marked increase in sensitivity to toxic effects of bacterial endotoxin. Sequential administration of Con A and endotoxin results in greater-than-additive hepatic injury (see Example 12A). Hepatocyte injury in viral and autoimmune hepatitis involves similar mechanisms, with damage initiated by T cells and exacerbated by enterally-derived endotoxin and other inflammatory processes.

TAU protects the liver of experimental animals from damage initiated by either endotoxin or Con A. In this experiment, TAU was tested for hepatoprotective effects in mice subjected to combined liver injury caused by sequential administration of both Con A and endotoxin.

Methods:

Female Balb/C mice (eight weeks old) were divided into three groups of seven animals each. One group of animals remained untreated to provide basal values for serum chemistry indices of tissue damage. Mice in the remaining two groups received 2 mg/kg Concancavalin A by intravenous (tail vein) injection in a volume of 0.2 ml saline, followed 24 hours later by *Salmonella Typhimurium* endotoxin (10 micrograms i.p.). One of these groups of mice received TAU (6000 mg/kg orally, in 0.6 ml of 0.5% methylcellulose two

TABLE 1

Concanavalin A potentiates endotoxin-induced tissue damage

| | ALT | AST | LDH | CPK | SDH |
|---|---|---|---|---|---|
| Basal | 87 ± 15 | 110 ± 9 | 656 ± 41 | 413 ± 87 | 39 ± 2 |
| Con A 2.5 mg/kg | 117 ± 19 | 170 ± 16 | 915 ± 46 | 419 ± 132 | 42 ± 4 |
| LPS 0.5 mg/kg | 119 ± 23 | 256 ± 22 | 881 ± 10 | 426 ± 82 | 41 ± 3 |
| Con A + LPS | 1130 ± 494 | 2119 ± 910 | 4370 ± 1303 | 1525 ± 450 | 471 ± 267 |

ALT = Alanine Aminotransferase
AST = Aspartate Aminotransferase
LDH = Lactate Dehydrogenase
CPK = Creatine Phosphokinase
SDH = Sorbitol Dehydrogenase Endotoxin or Con A alone at the doses used in this experiment produced minimal damage to liver and muscle as determined by serum enzyme levels (ALT, AST, LDH and hours before Con A and again 2 hours before endotoxin; the remaining Con A/endotoxin-treated group (Control) received vehicle (methylcellulose) alone. Eighteen hours after administration of endotoxin, blood samples were collected from all mice for determination of serum levels of various indices of tissue damage or metabolic dysfunction.

Results:

Sequential administration of Con A and endotoxin resulted in significant liver injury, as assessed by serum chemistry indices of liver damage. TAU, administered orally, markedly attenuates this combined liver injury.

| Oral TAU attenuates liver damage caused by Concanavalin A + LPS | | | | | |
|---|---|---|---|---|---|
| | ALT | AST | LDH | CPK | SDH |
| Basal | 118 ± 33 | 162 ± 14 | 522 ± 80 | 1521 ± 235 | 56 ± 3 |
| Con A/LPS | 2295 ± 309 | 3408 ± 389 | 5696 ± 560 | 4684 ± 1569 | 700 ± 69 |
| Con A/LPS + TAU | 285 ± 67* | 451 ± 87* | 1341 ± 236* | 2098 ± 465* | 122 ± 19* |

*= Different from Control (LPS i.p.), P < .02
ALT = Alanine Aminotransferase
AST = Aspartate Aminotransferase
LDH = Lactate Dehydrogenase
CPK = Creatine Phosphokinase
SDH = Sorbitol Dehydrogenase

Example 13

Oral Triacetyluridine Improves Recovery from Ethanol Intoxication

Ethanol intoxication results in depression of activity in the central nervous system. Recovery is dependent upon clearance of ethanol from the system. Ethanol clearance from the circulation occurs primarily in the liver, regulated by both the enzyme alcohol dehydrogenase and the redox balance and metabolic state of the liver.

In these experiments, ethanol-intoxicated mice were treated with triacetyluridine (TAU) in order to determine whether metabolic support through provision of uridine to the liver and other tissues affected recovery from ethanol intoxication.

Experiment 1: Fasted Mice

Methods:

Female Balb/C mice weighing an average of 22 grams were fasted for 24 hours. 9 mice received oral TAU 2000 mg/kg p.o., and 8 received vehicle (0.75% Hydroxypropylmethylcellulose in water).

One hour later, all animals received 5.7 ml/kg ethanol (0.5 ml of 25% aqueous solution p.o.).

One hour after EtOH, mice received an additional dose of TAU or vehicle. All mice were basically comatose at this time.

Behavior was monitored at hourly intervals, beginning 3 hours after ethanol administration. The scale for behavioral assessment is as follows:

Behavioral Recovery after Ethanol Intoxication

Deep coma: Unresponsive to stimuli. Slow respiration

Prostrate: Mice laying flat but not moving. Eyelid reflex to touching with a probe. Rapid respiration.

Righting reflex: When placed on its back, animal attempts to turn over within 5 seconds. Category includes all "mobile" animals and some "prostrate".

Mobile: Animal is capable of walking.

TAU Accelerates Recovery from Ethanol Intoxication in Fasted Mice

| Time | Dead | Deep coma | Prostrate | Righting Reflex | Mobile |
|---|---|---|---|---|---|
| Control n = 8 mice | | | | | |
| 3 hr | 1 | 8 | 0 | 0 | 0 |
| 4 hr | 1 | 5 | 3 | 0 | 0 |
| 5 hr | 2 | 3 | 3 | 3 | 0 |
| 6 hr | 2 | 2 | 2 | 4 | 2 |
| 7 hr | 2 | 1 | 1 | 4 | 4 |
| 8 hr | 2 | 1 | 1 | 5 | 4 |
| TAU n = 9 mice | | | | | |
| 3 hr | 0 | 5 | 4 | 4 | 0 |
| 4 hr | 0 | 4 | 5 | 4 | 0 |
| 5 hr | 0 | 2 | 7 | 6 | 0 |
| 6 hr | 0 | 1 | 1 | 7 | 7 |
| 7 hr | 0 | 1 | 0 | 8 | 8 |
| 8 hr | 0 | 0 | 1 | 8 | 8 |

Mice = Female Balb/C, 22 grams, fasted 24 hours
Ethanol dose = 5.7 ml/kg p.o. at time = 0 hr (0.7 ml of 25% EtOH)
TAU (2 g/kg) or vehicle (control group) were administered one hour before and one hour after ethanol Experiment 2: Non-Fasted Mice Female Balb/C mice weighing an average of 22 grams were allowed free access to food up to the time of the experiment. 10 mice received oral TAU 2000 mg/kg p.o., and 10 received vehicle (0.75% HPMC).

One hour later, all animals received 8 ml/kg ethanol (0.7 ml of 25% aqueous solution p.o.).

One hour after EtOH, mice received an additional dose of TAU or vehicle.

Behavior was monitored at intervals of 2,3,4, and 6 hours after ethanol administration. The scale for behavioral assessment was the same as in the test on fasted mice above.

TAU Accelerates Recovery from Ethanol Intoxication in Non-Fasted Mice

| Time | Dead | Deep coma | Prostrate | Righting Reflex | Mobile |
|---|---|---|---|---|---|
| Control n = 10 mice | | | | | |
| 2 hr | 0 | 9 | 1 | 0 | 0 |
| 3 hr | 0 | 7 | 3 | 2 | 0 |
| 4 hr | 1 | 1 | 6 | 5 | 2 |
| 6 hr | 1 | 0 | 1 | 8 | 8 |
| TAU n = 10 mice | | | | | |
| 2 hr | 0 | 5 | 5 | 2 | 0 |
| 3 hr | 0 | 1 | 5 | 5 | 3 |
| 4 hr | 0 | 0 | 3 | 8 | 7 |
| 6 hr | 0 | 0 | 0 | 10 | 10 |

Mice = Female Balb/C, 22 grams, fed ad libitum
Ethanol dose = 8 ml/kg p.o. at time = 0 hr (0.7 ml of 25% EtOH)
TAU (2 g/kg) or vehicle (control group) were administered one hour before and one hour after ethanol TAU clearly improved behavioral recovery in mice subjected to severe ethanol intoxication. Non-fasted mice were given a higher dose of ethanol than fasted animals (8 ml/kg versus 5.7 ml/kg), but nevertheless recovered somewhat faster. This observation highlights the importance of energy metabolism in recovery from ethanol intoxication. TAU accelerates recovery from ethanol intoxication in both fed and fasted animals.

Example 14

Triacetyluridine Reduces Mortality In Viral Hepatitis in Mice

Frog virus 3 (FV3) induces a rapidly fatal hepatitis in mice, which is mediated in part by secondary damage due to endogenous endotoxin (Gut et al., *J. Infect. Disease.,* 1984, 149:621).

Triacetyluridine (TAU) was tested in this model to demonstrate that this agent and other compounds of the invention have useful therapeutic effects in viral hepatitis.

Methods:

Lyophilized FV3 was reconstituted in phosphate-buffered saline to a density of $1\times10^8$ plaque-forming units (PFU) per ml.

Female Balb/C mice weighing 25 grams received FV3 virus at doses corresponding to the approximated $LD_{50}$ by intraperitoneal or intravenous (tail vein) injection. TAU (3000 mg/kg) or vehicle (0.75 hydroxypropylmethylcellulose) was administered orally one hour before FV3 and on subsequent afternoons and mornings. Animals were observed for three days; the animals that did not survive this observation period all died approximately 24–30 hours after virus administration.

| | Survival |
|---|---|
| Intraperitoneal administration of FV3 Virus: FV3 $4 \times 10^7$ PFU/mouse i.p. | |
| Control | 6/10 |
| TAU | 10/10 |
| Intravenous administration of FV3 Virus: FV3 $2 \times 10^7$ PFU/mouse i.v. | |
| Control | 5/10 |
| TAU | 10/10 |

The foregoing is intended as illustrative of the present invention but not limiting. Numerous variations and modifications may be effected without departing from the true spirit and scope of the invention.

What is claimed is:

1. A method for treating or preventing hepatic damage in an animal receiving parenteral nutrition comprising administering intravenously to said animal a therapeutically effective amount of a pyrimidine nucleotide precursor and including the further step of administering an inhibitor of uridine phosphorylase.

2. A method as in claim 1 wherein said hepatic damage is due to said animal receiving parenteral nutrition.

3. A method as in claim 1 wherein said pyrimidine nucleotide precursor is uridine, cytidine, orotic acid, or an acyl derivative of uridine, cytidine, or orotic acid, or a pharmaceutically acceptable salt thereof.

4. A method as in claim 1 wherein from 2 to 40 grams of said pyrimidine nucleotide precursor are administered per day.

5. A method for treating or preventing hepatic damage in an animal receiving total parenteral nutrition comprising administering to said animal an inhibitor of uridine phosphorylase.

* * * * *